US006749848B2

(12) United States Patent
Chen

(10) Patent No.: US 6,749,848 B2
(45) Date of Patent: Jun. 15, 2004

(54) **BIOLOGICAL CONTROL OF NEMATODES WITH *HIRSUTELLA MINNESOTENSIS***

(75) Inventor: Senyu Chen, Waseca, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/754,097

(22) Filed: Jan. 4, 2001

(65) Prior Publication Data

US 2001/0046485 A1 Nov. 29, 2001

Related U.S. Application Data

(60) Provisional application No. 60/174,402, filed on Jan. 5, 2000.

(51) Int. Cl.[7] ........................ A01N 63/00
(52) U.S. Cl. .................... 424/93.4; 435/254.1; 435/493
(58) Field of Search ........................ 424/93.5, 493; 435/254.1

(56) References Cited

U.S. PATENT DOCUMENTS 5,360,607 A * 11/1994 Eyal et al. ................. 424/93.5

FOREIGN PATENT DOCUMENTS

JP 60-253823 * 9/1994

OTHER PUBLICATIONS

Chen et al., "Pathogenicity of fungi to eggs of *Heterodera glycines*", J. Nematology 28 (2) : 148–158 (1996).*

Chen, S., et al., "Effects of Crop Sequence of Parasitism of *Heterodera Glycines* by *Hirsutella Rhossiliensis", Proceedings of the World Soybean Research Conference, VI*, Chicago, IL, pp. 610–611, (Aug. 1999).

Chen, S., et al., "*Hirsutella minnesotensis* sp. nov., a New Pathogen of the Soybean Cyst Nematode", *Mycologia, 92*(*5*), pp. 819–824, (2000).

Chen, S., et al., "Impact of Fungal Antagonists on SCN—A Minnesota Perspective", *National Soybean Cyst Nematode Conference*, p. 19, (Jan. 1999).

Chen, S., et al., "Parasitism of the Nematode *Heterodera glycines* by the Fungus *Hirsutella rhossiliensis* as Influenced by Crop Sequence", *Journal of Nematology, 31* (*4*), pp. 437–444, (1999).

Chen, S.Y., et al., "Investigation of Fungal Antagonists of *Heterodera Glycines* in Minnesota", *Journal of Nematology, 31* (*4*), Abstract, p. 527, (Dec. 1999).

Galper, S., et al., "Simple screening methods for assessing the predacious activity of nematode–trapping fungi", *Nematologica, 41*, pp. 130–140, (1995).

Jaffee, B., et al., "Density–Dependent Host–Pathogen Dynamics In Soil Microcosms", *Ecology, 73* (*2*), pp. 495–506, (1992).

Jaffee, B.A., et al., "Density–Dependent Parasitism of the Soil–Borne Nematode *Criconemella xenoplax* by the Nematophagous Fungus *Hirsutella rhossiliensis", Microb. Encol., 17*, pp. 193–200, (1989).

Jaffee, B.A., et al., "Detection of the Nematophagous Fungus *Hirsutella rhossiliensis* in California Sugarbeet Fields", *Biological Control, 1*, pp. 63–67, (1991).

Jaffee, B.A., et al., "Failure of a Mycelial Formulation of the Nematophagous Fungus *Hirsutella rhossiliensis* to Suppress the Nematode *Heterodera schachtii", Biological Control, 6*, pp. 340–346, (1996).

Jaffee, B.A., et al., "Suppression of Cyst Nematode by Natural Infestation of a Nematophagous Fungus", *Journal of Nematology, 21* (*4*), pp. 505–510, (1989).

Lackey, B.A., et al., "Alginate Pellet Formulation of *Hirsutella rhossiliensis* for Biological Control of Plant–Parasitic Nematodes", *Biological Control, 3*, pp. 155–160, (1993).

Liu, X.Z., et al., "Detection of the Nematophagous Hirsutella Species in Southern Minnesota Soybean Fields", *Journal of Nematology, 31* (*4*), Abstract, p. 551, (Dec. 1999).

Liu, X.Z., et al., "Preparation of *Heterodera glycines* by *Hirsutella spp.* in Minnesota Soybean Fields", *Biological Control, 19*, pp. 161–166, (2000).

Liu, X.Z., et al., "Screening Isolated of Hirsutella Species for Biocontrol of *Heterodera glycines", Biocontrol Science and Technology, 11*, pp. 151–160, (2000).

Müller, J., "The influence of fungal parasites on the population dynamics of *Heterodera schachtii* on oil radish", *Nematologica, XXVIII*, Abstract of Papers at the XVI$^{th}$ International Symposium, p. 161, (1982).

Tedford, E.C., et al., "Parasitism of *Heterdera schachtii* and *Meloidogyne javanica* by *Hirsutella rhossiliensis* in Microplots over Two Growing Seasons", *Journal of Nematology, 25* (*3*), pp. 427–433, (1993).

Timper, P., et al., "Infection of *Pratylenchus penetrans* by Nematode–pathogenic Fungi", *Journal of Nematology, 25* (*2*), pp. 297–302, (1993).

Velvis, H., et al., "Suppression of potato cyst nematode root penetration by the endoparasitic nematophagous fungus *Hirsutella rhossiliensis", Eurpean Journal of Plant Pathology, 102*, pp. 115–122, (1996).

Zehr, E.I., et al., "Evaluation of Parasites and Predators of Plant Parasitic Nematodes", *J. Agric. Entomol., 2*(*1*), pp. 130–134, (Jan. 1985).

* cited by examiner

*Primary Examiner*—Irene Marx
(74) *Attorney, Agent, or Firm*—Fish & Richardson, P.C., P.A.

(57) ABSTRACT

The present invention provides a novel isolated and purified fungus *Hirsutella minnesotensis.* The present invention also provides a pesticidal composition of an effective amount of an isolated and purified fungal strain of *Hirsutella rhossiliensis* or *Hirsutella minnesotensis* that is capable of controlling nematode infestation and a carrier. Further, the present invention provides methods of controlling nematode infestation.

3 Claims, 1 Drawing Sheet

BIOLOGICAL CONTROL OF NEMATODES WITH *HIRSUTELLA MINNESOTENSIS*

This application claims the benefit of provisional appl. No. 60/174,402 filed Jan. 5, 2000.

BACKGROUND OF THE INVENTION

The soybean cyst nematode (SCN), *Heterodera glycines,* is one of the most destructive plant-parasitic nematodes and has been found in most soybean-growing countries and regions in the world. The north central region of the United States is a major soybean-producing region and the nematode has been reported from all the states except North Dakota (Noel, 1992; Smolik, 1996). The nematode is a major yield-limiting factor of soybeans.

Management of the SCN has largely relied on rotation with non-host crops and planting resistant cultivars. In many cases, however, rotation and/or use of resistant cultivars are not efficient, or are impractical. Many factors including biotic and abiotic factors affect the efficacy of rotation and use of resistant cultivars. Results obtained in a recent crop rotation study indicated that 3 years of corn did not appear to be adequate to lower SCN density to a level where an SCN susceptible cultivar could be recommended in Minnesota. Further, increase of years of corn may result in corn yield penalty for the second and the following years for unknown reasons.

Use of resistant cultivars places a selection pressure on the nematode races. Continuous use of resistant cultivars with the same resistant source may result in race shift and eventually the resistance may be broken. Furthermore, the nematode can cause a significant yield loss even to resistant soybean cultivars. Therefore, it is important to reduce nematode density before planting a resistant cultivar.

Nematophagous fungi have been known for over 100 years and have been tested for biological control of plant parasitic nematodes for over 60 years (Linford, 1937; Zopf, 1888). Several fungi such as Arthrobotrys spp., *Drechmeria coniospora* (Drechsler) Gams & Jansson, *Hirsutella rhossiliensis* Minter & Brady, *Paecilomyces lilacinus* (Thom.) Samson, and *Verticillium chlamydosporium* Goddard, have been extensively studied but no successful biological control agents have been developed from these fungi (Galper et al., 1995; Stirling, 1991).

Nematophagous fungi have been isolated from various nematodes and locations. The fungi vary considerably among species and isolates in characteristics such as virulence to certain nematodes, colonization ability in plant roots, and competitive ability in soil (Boume et al., 1996; Timper and Riggs, 1998). The variability among isolates of *H. rhossiliensis, P. lilacinus,* and *V. chlamydosporium* has been demonstrated (Carneiro and Gomes, 1993; Irving and Kerry, 1987; Tedford et al., 1994). Waller and Faedo (1993) tested 94 species of nematode-trapping fungi for their infection of the free-living stage of animal-parasitic nematode, *Haemonchus contortus* Rudolphi in the sheep fecal environment and found only a few species with efficient activity.

*Hirsutella rhossiliensis* was first described in 1980 (Minter and Brady, 1980) based on a specimen collected from Wales in 1953. Sturhan and Schneider (1980) reported isolating this fungus from the hop cyst nematode, *Heterodera humuli* Filipjev, and named it *Hirsutella heteroderae* (synonym of *H. rhossiliensis*). The fungus has a wide range of hosts including plant-parasitic nematodes, free-living nematodes, entomopathogenic nematodes and mites, although different isolates may have different host preferences. *Hirsutella rhossiliensis* can parasitize a high percentage of nematodes in some locations. This fungus is probably an obligate parasite in nature and is generally isolated from only one species of nematode in a field (Jaffee and Zehr, 1985; Jaffee et al., 1991; Liu and Chen, 2000a; Sturhan and Schneider, 1980; Timper and Brodie, 1993; Velvis and Kamp, 1995).

*Hirsutella rhossiliensis* is a hyphomycetes with simple erect phialides which are swollen at the base and taper towards the apex. When a host nematode comes into contact with conidia on the phialides, the conidia can attach to the nematode cuticle, and infect the host nematode within a few days. Following penetration, the fungus forms an infection bulb in the nematode cavity, from which assimilative hyphae are developed. After converting nematode body contents to mycelial mass, the fungus may emerge from the nematode cadaver, produce spores, and infect other nematodes. An average of 112 conidia may be formed from mycelium developed from a single juvenile of *H. schachtii* at 20° C. (Jaffee et al., 1990). KCl increased infection of nematodes by the fungus (Jaffee and Zehr, 1983). Conidia detached from the phialides may lose infectivity. Some conidia died shortly after sporulation and others may be viable and virulent for at least 200 days (Jaffee et al., 1990). Variability of morphology, pathogenicity, and genetics was observed among isolates (Tedford et al., 1994).

Parasitism of nematodes by *H. rhossiliensis* is dependent on nematode density. The percentage of nematodes parasitized by the fungus correlates positively with host nematode density (Jaffee et al., 1992). The number of conidia attached to cuticle of nematode by *H. rhossiliensis* correlates with the amount of conidia in the soil. Since the fungus is a poor soil competitor, local populations of the fungus may go extinct unless supplied with some minimum number of nematodes (the host threshold density). Thus, natural epidemics of this fungus among populations of nematodes develops slowly and only after long periods of high host densities (Jaffee and Zehr, 1985). Transmission of spores is greater in loamy sand than in coarse sand (Jaffee et al., 1990). In contrast to the theory that addition of organic matter may enhance activity of some nematophagous fungi, addition of organic matter to soil decreases parasitism of *M. xenoplax* by *H. rhossiliensis* (Jaffee et al., 1994).

Many endoparasitic nematophagous fungi produce adhesive spores, which adhere to passing vermiform nematodes, and subsequently infect, and kill the host. *Drechmeria coniospora* (Drechsler) Gams & Jansson (Drechsler, 1941), *Hirsutella rhossiliensis* Minter & Brady (*Hirsutella heteroderae* Sturhan & Schneider, Sturhan and Schneider 1980; Jaffee and Zehr, 1982), and *Verticillium banaloides* Drechsler (Drechsler, 1941) are well known species in this group. Only *H. rhossiliensis,* however, parasitizes high percentages of nematodes in natural soils. The fungus parasitized 80% of *Mesocriconema xenoplax* Raski in California peach orchard soils (Jaffee et al., 1988) and 90% of *Heterodera schachtii* Schmidt J2 in oil-radish fields in Germany (Müller, 1982). *Hirsutella rhossiliensis* was naturally present in about 25% of the sugarbeet fields in Germany, in 17 of 20 fields in a starch-potato-growing area in the northeastern Netherlands (Velvis and Kamp, 1995), and in 10 of 21 sugarbeet fields in California, and may contribute to the suppression of *H.* schachtii (Müller, 1984, 1986; Jaffee et al., 1991; Juhl, 1985). Jaffee and Muldoon (1989) also found that penetration of cabbage roots by *H. schachtii* was suppressed by 50–77% in loamy sand naturally infested with *H. rhossiliensis. Hirsutella rhossiliensis* has been isolated from *Heterodera humuli* Filipjev (Sturhan and Schneider, 1980), *H.*

*schachtii* (Muller, 1984), *Heterodera avenae* Woll. (Stirling and Kerry, 1983), *Heterodera glycines* Ichinohe (Chen, 1997), *Meloidogyne javanica* (Treub) Chitwood (Cayrol et al., 1986), *M. xenoplax* (Jaffee and Zehr, 1982), *Rotylenchus robustus* (de Man) Filipjev (Jaffee et al., 1991), *Xiphinema diversicacaudatum* (Micoletzky) Thorne (Ciancio et al., 1986), *Hoplolaimus galeatus* Filip. & Schur. Stek., bacteria-feeding nematodes, soil mites, and soil (Tedford et al., 1994). It has also shown to infect *Ditylenchus dipsaci* (Kühn) Filipjev, *Aphelenchoides fragariae* (Ritz. Bos) Christie, *Meloidogyne incognita* (Kofoid & White) Chitwood (Cayrol and Frankowski, 1986; Cayrol et al., 1986), *Pratylenchus penetrans* (Cobb) Filip. & Schur. Stek (Timper and Brodie, 1993), Anguina sp. (Cayrol and Combettes, 1983), Anaplectus sp, Cephalobus (Sturhan and Schneider, 1980), and entomopathogenic species of Steinernema, Heterorhabditis (Timper et al., 1991) in laboratory and greenhouse studies.

The potential of the fungus as biological control agent has been controversial. Muller (1982) reported that the fungus might suppress cyst nematodes in some sugar beet fields in Germany. The fungus was considered to be partially responsible for suppression of *M. xenoplax* population in some orchards in the southern United States (Zehr, 1985). High numbers and percentages of *M. xenoplax* parasitized by *H. rhossiliensis* were also found in some California peach orchards (Jaffee et al., 1989). In greenhouse studies, *H. rhossiliensis* suppressed *G. pallida* on potato (Velvis and Kamp, 1996), *H. schachtii* on cabbage (Jaffee and Muldoon, 1989), and *Pratylenchus penetrans* Cobb on potato (Timper and Brodie, 1994).

Results obtained by Tedford et al. (1993), however, indicated that long-term interactions between populations of *H. rhossiliensis* and cyst or root-knot nematodes will not result in biological control. In a field microplot test, *H. rhossiliensis* failed in suppression of *H. schachtii* (Jaffee et al., 1996). *H. rhossiliensis* has been formulated in alginate pellets and used in control of nematodes in laboratory or greenhouse studies (Lackey et al., 1993; Jaffee et al., 1996). No commercial formulation, however, has yet been developed.

Biological control represents one of the components in an integrated pest management program and has been shown promise in control of many other agricultural pests. Especially in view of bans on chemical nematicides, such as the ban on methyl bromide, there remains a continuing need for a means to safely and effectively control the spread of nematodes, specifically of *Heterodera glycines*. Further, there is a long-felt, unresolved need to produce a pesticidal composition that can be sprayed, or similarly applied, onto crops to control nematodes.

SUMMARY OF THE INVENTION

The present invention provides a novel isolated and purified strain of fungus *Hirsutella minnesotensis*. The *H. minnesotensis* may be capable of controlling plant-parasitic nematodes, such as the nematode *Heterodera glycines*, and/or other agricultural pests. The *H. minnesotensis* may be culture deposit ATCC MYA-31 (CBS 102348) or any other isolate of the species such as isolates CBS 102457, CBS 102458 or CBS 102459.

The present invention also provides a pesticidal composition comprising an effective amount of an isolated and purified fungal strain of *Hirsutella rhossiliensis* or *Hirsutella minnesotensis* capable of controlling nematode infestation, and a carrier. The nematode may be a plant-parasitic nematode, such as *Heterodera glycines*, but is not limited to *H. glycines*. The *Hirsutella rhossiliensis* may be isolate OWVT-1, specifically culture deposit ATCC PTA-3179. which was deposited in the Amencan Type Culture Collection (ATCC), 10801 University Blvd., Manassas, Va. 20110 on Mar. 14. 2001. The *H. minnesotensis* may be culture deposit ATCC PTA-3180 (CBS 102348), which was denosited in the American Type Culture Collection (ATCC), 10801 University Blvd., Manassas, Va. 20110 on Mar. 14, 2001, or other isolate. The carrier may be diatomaceous earth, alginate, clay, or other plant and animal products as solid formulations. Alternatively the carrier may be a liquid form. An adjuvant or activator may be added into the solid or liquid formulations. Such an adjuvant or activator may increase dispersal, vegetative growth, sporulation, spore germination of the fungus, and/or inhibit soil microbial competitors. The activator may be in a monosaccharide, disaccharide, polysaceharide, amino acid, peptide, peptone, protein, vitamin, other organic compound, or inorganic salt. The Hirsutella strain may be in the spore and/or mycelium form. The pesticidal composition may contain an effective amount of at least one strain of *Hirsutella rhossiliensis* or *Hirsutella minnesotensis* that is in the range of about 1×102 to about $1\times10^{12}$ spores or colony forming units (cfu) per milliliter of liquid culture or per gram of solid culture. Alternatively, it maybe in the range of about $1\times10^4$ to about $1\times10^9$ spores or cfu per ml or gram, or even in the range of about $1\times10^5$ to about $1\times10^8$ spores or cfu per ml or gram.

The present invention further provides method for controlling nematodes comprising applying an effective amount of a pesticidal composition onto a target plant or onto the situs of a target plant (i.e., the area around the target plant), wherein the pesticidal composition comprises an effective amount of an isolated and purified fungal strain of *Hirsutella rhossiliensis* or *Hirsutella minnesotensis* capable of controlling nematode infestation and a carrier. The pesticidal composition is applied at least once, but may be applied a plurality of times in a single growing season, or over the course of several growing seasons.

DETAILED DESCRIPTION OF THE INVENTION

Figure 1:
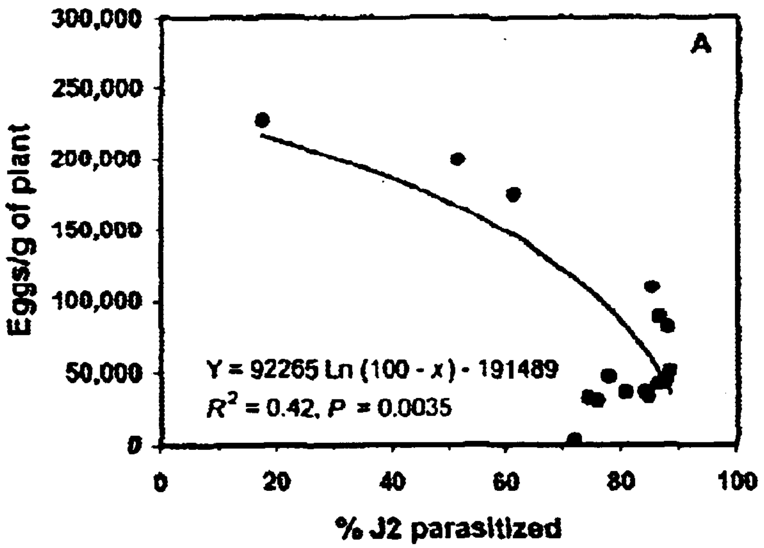
FIG. 1. Relationship between nematode density in greenhouse pots and parasitism of second-stage Juveniles (J2) of *Heterodera glycines* by *Hirsutella rhossiliensis* and *Hirsutella minnesotensis* on agar (A) and in soil in laboratory (B).
Figure 1:
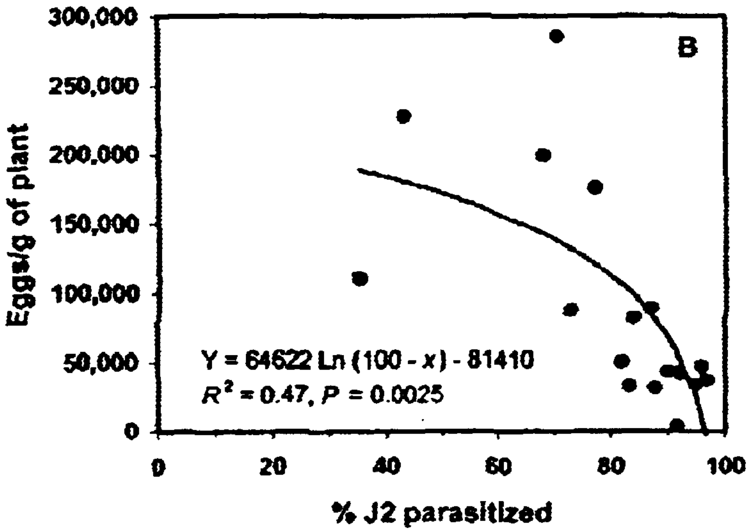

Natural enemies of nematodes include fungi, bacteria, viruses and some microscopic animals such as insects, mites, and nematodes. Nematophagous fungi include trapping fungi that form special devices to capture and kill nematodes, endoparasites of vermiform nematodes, fungi colonizing eggs and females of sedentary endoparasitic nematodes, and fungi that are antibiotic to nematodes. Most Hirsutella species are parasites of insects and mites. Only *H. rhossiliensis* and the fungus *Hirsutella minnesotensis*, newly discovered by the present inventors, have been seen to parasitize nematodes.

*Hirsutella minnesotensis* Chen et al. is a major parasite of the second-stage juveniles (J2) of soybean cyst nematode (SCN), *Heterodera glycines* Ichinohe. It has similar characteristics of *H. rhossiliensis* (Chen et al., 2000; Liu and Chen, 2000a). *Hirsutella minnesotensis* was isolated from SCNJ2 collected from a soybean field with a low SCN density (Chen et al. 2000).

Studies were performed to determine distribution, frequency occurrence of Hirsutella species in soybean fields in the north central region in the United States. Previous reports demonstrated that adding host nematodes into soil increased detection of the *H. rhossiliensis* in sugar beet fields (Jaffee et al., 1991). For this reason, baiting methods were used by adding SCN J2 into the soil samples as well as direct detection methods. *Hirsutella minnesotensis* was observed in 14% (34 of 237) fields in 27 counties in southern Minnesota. The fungus was also detected in South Dakota, Michigan, and Iowa, but not in Missouri, Kansas, and Wisconsin. The fungus appeared to be highly pathogenic to SCN and parasitized a high percentage of J2 in some fields. In a field trial in 1998, *H. minnesotensis* reduced egg density by 58% at the end of the season, which was similar to the efficacy of the nematicide aldicarb (64% reduction); and *H. rhossiliensis* reduced egg density by 32%. In 1999, average yield treated with *H. rhossiliensis* was 6.2 and 7.0 bu/A higher than average of control at two sites; average yield treated with *H. minnesotensis* was 4.5 bu/A higher than control at one site. In 2000, *H. minnesotensis* reduced egg density by 39% at the end of the season, and *H. rhossiliensis* reduced egg density by 20%. The present data indicate that the fungus is effective as a biocontrol agent.

Studies were also performed to screen isolates of *H. rhossiliensis* and *H. minnesotensis* on agar, in soil, and under greenhouse conditions for their use as biological control agents against *Heterodera glycines.*

Further, the relationship between J2 density and percentage of J2 parasitized by *H. rhossiliensis* was investigated in plots with a wide range of nematode densities generated with various sequences of soybean cultivars. The J2 density and percentage of J2 parasitized by the fungus were measured. A significant positive relationship between the J2 density and percentage of J2 parasitized by the fungus was observed at the early season and in late season, when there were broad ranges of the nematode densities in the plots. The results also indicate that the fungal population increased when nematode increased on susceptible cultivars. The increased fungal population, in return, suppressed nematode population density. Thus, the fungus was effective in regulating the nematode population.

Mycopesticide Formulations

The novel mycopesticide of the present invention can be used effectively in diverse formulations, including the agronomically acceptable carriers and adjuvants or activators normally employed for facilitating the activity of ingredients for agriculture applications, recognizing a known fact that the dosage, formulations, mode of application of a chemical agent and other variable may affect its activity in any given application. The described mycopesticide can be formulated as a suspension or dispersion, in aqueous or non-aqueous media, as a dust, as a wettable powder, as a granule, or as any of several other known types of formulations, depending on the desired mode of application. These pesticide compositions can be applied as sprays, dusts, or granules directly to a plant or its situs where pesticidal activity is desired.

The subject fungus, *H. minnesotensis* or *H. rhossiliensis,* can be obtained by conventional culture techniques from deposited culture specimens. To convert it to a form that will facilitate the preparation of the following described compositions, a slurry can be prepared that can then be formulated onto a primary agronomically acceptable carrier, e.g., vermiculite, whereby the fungus is incorporated or capsulated onto the carrier. If desired, the slurry can be used as the concentrate for the pesticidal composition. The actual concentration of propagules in the formulated composition is a function of practical consideration such as the properties of the vehicle or carrier, and the method of application. Certain spore or mycelium concentrations, which are described herein, however, have been found to be preferred. For purposes of formulation and application, an "effective amount" is defined to mean any such quantity of propagules sufficient to infect the target pest and thereby induce the lethal activity described herein.

The subject material described herein can be applied to a region to be treated by applying it directly to the soil as pre-emergence treatment or as post-emergence treatment, or it can be mixed intimately with the soil. The preferred mode of treatment is application before emergence of the plant foliage. The subject materials described herein can, for example, be applied to soil in amounts of about 0.1 gallons per acre to 300 gallons per acre, wherein the composition is at a concentration of about $1\times10^4$ to about $1\times10^{12}$ spores/cfu per ml as a liquid formulation, or of about 1 lb to about 1,000 lb per acre, wherein the composition is at a concentration of about $1\times10^4$ to about $1\times10^{12}$ spores/cfu per gram as a solid formulation.

As used herein, an "pesticidally effective" amount of the fungal agent is an amount that is sufficient to control nematode infestation. "Controlled" infestation is intended to mean the ability of the fungus according to the present invention to control nematode infestation to a degree sufficient to reduce or prevent the ability of nematodes to detrimentally affect the growth of the surrounding plants. However, "controlled" infestation does not necessarily require the complete eradication of all of the nematodes in an area.

Fungal Agents

The pesticidal composition of the invention is an effective pesticidal amount of at least one pathogenic fungal agent capable of controlling nematode infestation, such as *Helerodera glycines,* combined with an agricultural carrier. The fimgal agent is a strain of *Hirsutella rhossiliensis* or *Hirsutella minnesotensis.* The *Hirsutella rhossiliensis* may be isolate OWVT-1, specifically culture deposit ATCC no. PTA-3179. The *H. minnesotensis* may be culture deposit ATCC PTA 3180, or other isolates of the species. growing from a nematode cadaver, and purifying the fungus. The fungus may be maintained on various agar media.

Suitable Carriers

The fungal agent is combined with a suitable carrier in an effective pesticidal concentration. Examples of suitable carriers include water, fertilizers, plant-based oils, humectants, or combinations thereof. Alternatively, the agricultural carrier may be a solid, such as diatomaceous earth, alginate, clay, other plant and animal products, or combinations, including granules or suspensions. Alternatively, the liquid may be modified to yield a physiological solution. Suitable physiological solutions include sodium phosphate, sodium chloride, sodium acetate, sodium citrate and the like, preferably in an about 0.001-1 M aqueous phosphate buffer. Other suitable physiological solutions are well known in the art and would include 0.85% sodium chloride. An effective pesticidal amount of the fungal agent is at about $10^2$ to $10^{12}$ spores or cfu per ml or per gram. Alternatively, the concentration is at about $10^4$ to $10^9$, and even at about $10^5$ to $10^8$ spores or cfu per ml of a liquid medium or per gram of a solid medium.

Adjuvants and Germination Activators

An adjuvant or activator may be added to the pesticidal composition of the present invention. The adjuvant or activator provides better fungal activities. Preferred adjuvants or activators are those that have low phytotoxicity, such as methylated seed oils.

The adjuvant is dispersed in a liquid suspension containing the fungal agent to yield the present pesticidal composition. The adjuvant is present in an effective plant tissue-penetrating amount that is preferably within the range of about 0.001% to 10% volume/volume, more preferably about 0.01% to 6% volume/volume, and most preferably about 0.1% to 4% volume/volume of the liquid suspension containing the fungal agent.

The pesticidal composition may also contain an activator. Examples include monosaccharides, disaccharides, polysaccharides, amino acids, peptides, peptones, proteins, vitamins, inorganic salts, and other solutes.

Methods of Forming and Using the Pesticidal Composition

The pesticidal composition is useful to control nematodes in a variety of environments, especially croplands. The present pesticidal composition is formed by combining an effective amount of at least one strain of a fungal agent with an agricultural carrier, and optionally with an adjuvant and/or an activator, to form an essentially homogeneous dispersion.

After the pesticide is formulated, it is applied to the nematode-infested area. The pesticidal mixture may be applied by ground spraying, aerial spraying, painting or brushing, or by hand or mechanical dispersion, including but not limited to backpack or other hand held devices, hydraulic or air nozzles, granular applicators, electrostatic applicators, controlled droplet applicators (CDA), or ultra-low volume (ULV) applicators. The pesticidal composition may also be suitable for application by low pressure spraying so that large areas of land may be easily treated.

The pesticidal mixture is applied in single or repeated applications until nematode infestation is effectively inhibited. The conditions leading to effective nematode inhibition depend, in part, on the environment. For example, a single application of the pesticidal mixture may be sufficient or a plurality of applications may be required. The pesticidal composition of the present invention can be applied to soil, bare ground, plant litter or to plants of any age, including plants that have flowered or senesced. The pesticidal mixture is applied at a density sufficient to cover the area where nematode growth is expected to be observed in amounts from about 0.1 gallons per acre to 300 gallons per acre, wherein the composition is at a concentration of about $1\times10^2$ to about $1\times10^{12}$ spores or cfu per ml in a liquid medium, or equivalent in a solid medium. The concentration may be in the range of $10^4$ to $10^9$ spores per ml, or in the range of $10^5$ to $10^8$ spores per ml. Nematode growth is effectively inhibited if the majority of nematodes are infected with the fungal agent and exhibit symptoms of disease.

The following examples are intended to illustrate but not limit the invention.

EXAMPLE 1

Distribution and Frequency Occurrence of Hirsutella Species

A survey was conducted to determine the extent of infestation of soybean fields by the fungus Hirsutella in southern Minnesota (Liu and Chen, 2000a). A total of 264 soil samples representing 237 fields in 27 counties were examined in three experiments. In Test 1, 1,000 J2s were added to 50 grams of soil at days 0, 7, 14, and 21, and the nematodes were recovered at day 28. In Test 2, 2,000 J2s were added to 50 $cm^3$ of soil and the nematodes were recovered at day 14. In Test 3, J2s were extracted from 50 $cm^3$ of soil without addition of nematodes. The J2 were examined with an inverted microscope at magnifications of 40-200× for fungal infection. J2 colonized by the fungal mycelium or J2 with attached Hirsutella spores were considered parasitized. Fungi were isolated from 5 to 15 colonized J2 in each soil for identification to species. Two species of Hirsutella, i.e., *H. rhossiliensis* and *H. minnesotensis,* were commonly encountered on J2. Combining data from all three tests, parasitism of J2 by Hirsutella species was observed in soil from 46% of fields. Parasitism of J2 by *H. rhossiliensis* was observed in soil from 43% of fields and by *H. minnesotensis* in soil from 14% of fields. The highest percentage of J2 parasitized by Hirsutella spp. was 60%. Addition of J2 into soil increased efficiency of detection of the fungal parasitism.

Collection ofsoil samples: About 1,000 soil samples were collected from soybean fields across southern Minnesota and had been used for estimating the SCN infestation in the area. Generally, each soil sample was taken from soybean root zone with a soil probe or shovel to a depth of 15 to 20 cm in a zigzag pattern in an area of about 5 hectares. From these samples, a total of 264 soil samples (representing 237 fields in 27 counties) were randomly selected and used for the survey of fungal parasites of SCN J2. In a few fields, more than one soil sample from different areas in the same field were included.

Test 1: Fifty grams of soil were taken from each of 212 soil samples, that had been stored in refrigerators (4° C.) for 2 weeks to 6 months, and placed into a 240-ml plastic box (70 mm×70 mm×50 mm deep) (Neatway Products Inc., Minneapolis, Minn.). *Heterodera glycines* was cultured on soybean in autoclaved sandy soil for about 2 months in a growth room at about 25° C. Newly formed females and cysts were washed with a vigorously applied water stream through an 800-$\mu$m-aperture sieve onto a 250-$\mu$m-aperture sieve and extracted by centrifugation in 76% (w/v) sucrose solution. Eggs were released from the cysts by breaking the cysts in a 40-ml glass tissue grinder (Fisher catalogue No. 08-414-10D or equivalent). The eggs were separated from debris by centrifugation in 35% (w/v) sucrose solution for 5 minutes at 1,500 g. They were treated with a solution containing 100 mg streptomycin, 50 mg of chlortetracycline, and 20 mg of quinolinol per liter of deionized water and stored at 4° C. until used for hatching J2. Before hatching, the eggs were rinsed with deionized water and placed in a 4 mM $ZnCl_2$ solution. Within 2 days the hatched J2 were collected and rinsed with sterile deionized water. About 1,000 SCN J2 in 1 ml water were added into each box on the surface of soil at days 0, 7, 14, and 21. The boxes were covered with lids to avoid loss of soil moisture and to prevent contamination. They were maintained at room temperature (22–24° C.) under ambient lights.

For preparation of soybean root exudates, soybean plants that had been grown in a growth room for 3 weeks were removed from 15-cm-diameter pots and soybean roots were washed with water. About 50 plants were placed in a beaker and 300 ml of sterile deionized water was added. After 48 hours, the solution of the root exudates was collected and passed through a 0.45-$\mu$m-pore filter. Fourteen days after first adding the J2, a 1 ml aliquot of soybean root exudate was added into the soil surface in each of the boxes to encourage hatching of eggs of naturally occurring SCN populations in the soil.

At day 28, J2 were extracted using a sucrose-flotation and centrifuigation method (Jenkins, 1964). The suspension of nematodes from each soil sample was adjusted to 15 ml and stored at 4° C. in a refrigerator until examination. Each nematode suspension was subsequently placed in one well of 6-well tissue culture plate and examined at a magnification of 40× to 10× with an inverted microscope. Total J2 and J2 parasitized by *H. rhossiliensis* and/or *H. minnesotensis* were counted. J2 with attached fungal spore(s) or filled with mycelium were considered parasitized. Parasitism of J2 by the two species was distinguished by size and appearance of conidia attached to the nematode cuticle or conidia developing on mycelium growing from a nematode cadaver. To confirm parasitism of J2 by the two species, five to 15 J2 with attached fungal spores or filled with mycelium were handpicked from each infested soil sample with a needle made from bamboo and placed on potato dextrose agar (PDA, Difco, Detroit) or corn meal agar (CMA, Difco, Detroit) plates containing 100 mg streptomycin sulfate and 50 mg chlortetracycline per liter of medium for fungal identification.

In this test, where the J2 were added weekly, *H. rhossiliensis* was observed in 77 out of 212 samples (36%), *H. minnesotensis* was observed in 22 samples (10%), and both fungi were observed in 10 samples (5%) (Table 1). The highest percentages of J2 parasitized by *H. rhossiliensis* and *H. minnesotensis* in a single soil sample were 50% and 35%, respectively.

TABLE 1

Frequency occurrence of *Hirsutella rhossiliensis* (*Hr*) and/or *Hirsutella minnesotensis* (*Hm*) in soils collected from soybean fields infested or not infested by *Heterodera glycines* in each county in southern Minnesota.

| | Experiment 1[a] | | Experiment 2[a] | | Experiment 3[a] | | Total soil samples[b] | | Total fields[c] | |
|---|---|---|---|---|---|---|---|---|---|---|
| County | No. of samples examined | No. of samples with fungi | No. of samples examined | No. of samples with fungi | No. of samples examined | No. of samples with fungi | No. of samples examined | No. of samples with fungi | No. of fields examined | No. of fields with fungi |
| Blue Earth | 5 | 1 | 2 | 0 | 1 | 0 | 6 | 1 | 3 | 1 |
| Brown | 22 | 4 | 6 | 1 | 7 | 4 | 24 | 5 | 22 | 5 |
| Carver | 2 | 0 | | | | | 2 | 0 | 2 | 0 |
| Chippewa | 1 | 0 | | | | | 1 | 0 | 1 | 0 |
| Cottonwood | 3 | 0 | 4 | 0 | | | 5 | 0 | 5 | 1 |
| Dodge | 2 | 0 | 2 | 0 | 1 | 0 | 4 | 0 | 2 | 0 |
| Faribault | 8 | 4 | 10 | 9 | 12 | 1 | 15 | 12 | 15 | 12 |
| Fillmore | 8 | 2 | | | 4 | 0 | 8 | 2 | 8 | 2 |
| Freeborn | 9 | 5 | 4 | 3 | 6 | 1 | 11 | 7 | 11 | 7 |
| Goodhue | 1 | 1 | 2 | 0 | 1 | 0 | 2 | 1 | 2 | 1 |
| Jackson | 27 | 12 | 8 | 3 | 12 | 5 | 25 | 11 | 25 | 11 |
| Le Sueur | 5 | 3 | | | 4 | 0 | 5 | 3 | 2 | 2 |
| Lincoln | 2 | 0 | | | | | 2 | 0 | 2 | 0 |
| Martin | 20 | 7 | 11 | 9 | 15 | 5 | 30 | 13 | 23 | 12 |
| Mower | 1 | 1 | 3 | 0 | 1 | 1 | 3 | 1 | 3 | 1 |
| Nicollet | 4 | 1 | | | 1 | 0 | 4 | 1 | 3 | 1 |
| Nobles | 2 | 0 | 3 | 0 | | | 3 | 0 | 1 | 0 |
| Olmsted | 12 | 2 | 3 | 0 | 3 | 0 | 12 | 1 | 12 | 1 |
| Redwood | 3 | 3 | 6 | 1 | 4 | 0 | 7 | 4 | 7 | 4 |
| Rice | | | 1 | 0 | | | 1 | 0 | 1 | 0 |
| Scott | 1 | 0 | 1 | 0 | | | 2 | 0 | 1 | 0 |
| Steel | 7 | 6 | 7 | 6 | 9 | 5 | 12 | 9 | 11 | 9 |
| Sibley | 2 | 0 | 4 | 0 | | | 6 | 0 | 6 | 0 |
| Swift | 2 | 0 | 1 | 0 | | | 2 | 0 | 2 | 0 |
| Waseca | 23 | 14 | 12 | 5 | 15 | 2 | 30 | 17 | 28 | 14 |
| Winona | 2 | 0 | | | | | 2 | 0 | 2 | 0 |
| Watonwan | 38 | 24 | 8 | 6 | 26 | 13 | 40 | 26 | 37 | 25 |
| Total | 212 | 90 | 98 | 43 | 122 | 37 | 264 | 114 | 237 | 109 |
| % of samples with *Hr* and/or *Hm* | | 42 | | 44 | | 30 | | 43 | | 46 |
| % of samples with *Hr* | | 36 | | 43 | | 28 | | 40 | | 43 |
| % of samples with *Hm* | | 10 | | 10 | | 4 | | 13 | | 14 |
| % of samples with *Hr* and *Hm* | | 5 | | 9 | | 2 | | 9 | | 11 |

<sup>a</sup>In Experiment 1, 1,000 second-stage juveniles (J2) of *Heterodera glycines* were added into 50 grams of soil at days 0, 7, 14, and 21, and the nematodes were recovered at day 28 for examining parasitism of J2 by fungi. In Experiment 2, 2,000 J2 were added into 50 cm$^3$ of soil at day 0 and the nematodes were recovered at day 14 for examining parasitism of J2 by fungi. In Experiment 3, J2 were extracted from 50 cm$^3$ of soil directly for examining parasitism of J2 by fungi.

<sup>b</sup>If the same soil sample was used in the three experiments, it was counted one time. When Hr and/or Hm were observed in either experiment, the soil was considered positive for infestation.

<sup>c</sup>In a few fields, more than one soil sample from different areas in a same field were examined. Soil samples from the same field were counted as one field. When Hr and /or Hm in either soil samples from a same field were observed in either experiment, the field was considered positive for infestation.

Test 2: Forty-three soil samples that had been used in Test 1 and another 55 soil samples randomly selected from the 1,000-sample poll were studied. Fifty cm$^3$ soil from each sample were placed individually in 250-ml beakers and 2,000 J2 were added to the soil surface. The beakers then were covered with aluminum foil and maintained at room temperature (22–25° C.) for 2 weeks. Nematodes were extracted and the percentage of J2 parasitized by fungi was determined following the procedures described above.

In this second test, where 2,000 J2 were added into soil one time, *H. rhossiliensis* was observed in 43 out of 98 samples (43%), *H. minnesotensis* was observed in 10 samples (10%), and both fungi were observed in 9 samples (9%) (Table 1). The highest percentage of J2 parasitized by *H. rhossiliensis* in a single soil sample was 60%.

Test 3: Ninety-six soil samples in which Hirsutella spp. had been found in Test and 2 were used in this study. An additional 26 soil samples randomly selected from the 1,000-sample poll were included. A subsample of 50 cm$^3$ soil was taken from each soil and J2 were extracted from the soil without addition of nematodes. The percentage of J2 parasitized by the fungi was determined using the procedures described above.

In this third test, where J2 were extracted directly from the soil samples, *H. rhossiliensis* was observed in 34 out of 122 samples (28%), *H. minnesotensis* was observed in 5 samples (4%), and both fungi were observed in 2 samples (2%) (Table 1). The highest percentage of J2 parasitized by Hirsutella spp. was 36%.

*Hirsutella rhossiliensis* was also observed on other nematodes (mainly bacteria-feeding nematodes) in 20 samples, of which 15 samples contained SCN J2 parasitized by Hirsutella spp. Infection of SCN males by *H. rhossiliensis* and *H. minnesotensis* was also observed.

Other fungal parasites of J2 were also isolated, including *Monacrosporium drechsleri* Tarjan (in nine samples), *Hyphochytridium catenoides* Karling (which has not been reported from nematodes previously), *Verticillium banaloides* (Drechsler) Dowsett, Reid & Hopkin, *Nematoctonus hamatus* Thorn & Barron, and unidentified zoosporic and sterile fungi. These fungi parasitized fewer than 1% of J2.

Hirsutella species were detected by directly examining the SCN J2 that had been attached with fungal spore(s) and/or filled with hyphae rather than by using the method of plating nematode suspensions on agar as described in a previous report (Jaffee et al., 1991). It was assumed that J2 attached with one or more Hirsutella spores would be eventually infected. This assumption is based on the observation in a previous study that a single *H. rhossiliensis* conidium attached to *Ditylenchus dipsaci* was sufficient for infection (Cayrol and Frankowski, 1986). Although the possibility could not be excluded that the attached spore would not infect the SCN J2 and the J2 would be attached by other fungal spores and filled by other fungal hyphae, this possibility was low. First, J2 were filled by distinct hyphae after infection by Hirsutella spp, but were filled by hyphal fragments, spores, or sporangia after infection by zoosporic fungi. Second, in the present study about 500 isolates of Hirsutella spp. were obtained, but only a few isolates of sterile or other fungi were isolated. This indicated that J2 with attached conidia or filled with mycelium were generally parasitized by Hirsutella spp. Finally, morphology and size of spores of the two Hirsutella are distinct from each other and no other fungi with similar spores were isolated from the nematode.

Hirsutella species were detected in 6 of 53 (11%) samples in which SCN was not detected, while they were found in 98 of 190 (52%) samples that had been infested by SCN. Since the parasitism of nematode by *H. rhossiliensis* is dependent on host density (Jaffee et al., 1992), the fungal population is easier to detect in fields with high nematode densities than in fields with low nematode densities. In those fields where the fungi were not detected, the fungi may not have been introduced or have not established due to the low host nematode population density or absence of the host nematode. It is also possible that the fungi existed in a field but were not in the sampled soil due to limited volume of soil and area sampled. Hirsutella species have been detected in 17 of 27 counties in Minnesota. Hirsutella species may be present in the remaining 10 counties but were not detected due to limited number of soil samples examined in those counties.

The baiting methods (Tests 1 and 2) were more effective for detecting Hirsutella species in SCN J2 than the method of direct extraction (Test 3) especially for *H. minnesotensis*, agreeing with the previous report on *H. schachtii* (Jaffee et al., 1991). Similar percentages of soil samples with infection of Hirsutella spp. were detected by periodic additions (Test 1) and one-time addition (Test 2) of a large number of *H. glycines* J2 (Tables 1 and 2). Forty-three samples were used in both Test 1 and Test 2. Thirty-five out of the 43 soil samples had the same results in both experiments. Results of eight soil samples differed in Experiments 1 and 2, i.e., Hirsutella species were found in six samples in Test 1 but not in Test 2, and Hirsutella species were found in two samples in Test 2 but not in Test 1. Hirsutella spp. were found only in 30% of the samples with direct extraction in Test 3, although 96 samples used in Test 3 had been found with infection of Hirsutella spp. in Experiments 1 and 2. *Hirsutella minnesotensis* was detected in 4% of soil samples in Test 3, as compared with 10% in Experiments 1 and 2. The highest percentage of parasitized J2 in a sample detected by the direct method (36%) was lower than that detected by baiting methods (50% and 60% in Experiments 1 and 2, respectively).

TABLE 2

Frequency distribution of the parasitism of *Heterodera glycines* second-stage juveniles (J2) by *Hirsutella rhossiliensis* and/or *H. minneostensis* in soils from southern Minnesota.

| Percentage of J2 parasitized | Experiment 1[a] No. of samples | Experiment 1[a] % of samples | Experiment 2[a] No. of samples | Experiment 2[a] % of samples | Experiment 3[a] No. of samples | Experiment 3[a] % of samples | Total No. of samples | Total % of samples |
|---|---|---|---|---|---|---|---|---|
| 0 | 122 | 57.5 | 55 | 56.1 | 86 | 70.5 | 263 | 60.9 |
| 0.1–10 | 52 | 24.5 | 30 | 30.6 | 30 | 24.6 | 112 | 25.9 |
| 11–20– | 19 | 9.0 | 8 | 8.2 | 2 | 1.6 | 29 | 6.7 |
| 21–30 | 7 | 3.3 | 3 | 3.1 | 3 | 2.5 | 13 | 3.0 |
| 31–40 | 9 | 4.2 | 0 | 0 | 1 | 0.8 | 10 | 2.3 |
| 41–50 | 3 | 1.4 | 1 | 1.0 | 0 | 0 | 4 | 0.9 |
| 51–60 | 0 | 0 | 1 | 1.0 | 0 | 0 | 1 | 0.2 |
| >61 | 0 | 0 | 0 | 0 | 0 | 0 | 0 | 0 |
| Total | 212 | 100 | 98 | 100 | 122 | 100 | 432 | 100 |

[a]In Experiment 1, 1,000 second-stage juveniles (J2) of *Heterodera glycines* were added into 50 grams of soil at days, 0, 7, 14, and 21, and the nematodes were recovered at day 28 for examining parasitism of J2 by fungi. In Experiment 2, 2,000 J2 were added into 50 cm3 of soil at day 0 and the nematodes were recovered at day 14 for examining parasitism of J2 by fungi. In Experiment 3, J2 were extracted from 50 cm3 of soil directly for examing parastism of J2 by fungi.

The host range of *H. rhossiliensis* is relatively broad and may even include soil mites (e.g., Sturhan and Schneider, 1980; Tedford et al., 1994). In any given field, however, the fungus is generally isolated from only one species of host, although many other species of nematodes are present (Jaffee et al., 1991). *Hirsutella rhossiliensis* and/or *H. minnesotensis* were found only in SCN J2 in most soil samples in the present study, but *H. rhossiliensis* also was found in bacteria-feeding nematodes in a few samples. The morphology and nutrition requirements of *H. rhossiliensis* from bacteria-feeding nematodes were somewhat different from that isolated from SCN. There was no significant difference in morphology between Hirsutella spp. from SCN J2 and from SCN males. Morphological, pathogenic, and genetic variability among isolates of *H. rhossiliensis* has been demonstrated (Tedford et al., 1994). The growth rate of *H. rhossiliensis* isolates from SCN and bacteria-feeding nematodes were observed to be slower than that of the isolate (ATCC 46487) from *M. xenoplax.*

In summary, *Hirsutella rhossiliensis* and *H. minnesotensis* were the most common species and either or both species were detected in 17 of 27 counties in Minnesota where SCN occurs. Parasitism of SCN J2 by Hirsutella species was observed in 43% of the 264 soil samples and 46% of the 237 fields. *Hirsutella rhossiliensis* was detected in 40% of soils and 43% of fields and *H. minnesotensis* was detected in 13% of soil samples and 14% of fields. Nine percent soil samples and 11% of the fields had both fungi (Table 1). About 13% samples were encountered with over 10% of J2 parasitized by Hirsutella spp. and the highest percentage of J2 parasitized by Hirsutella spp. was 60% (Table 2).

EXAMPLE 2

Detection of Hirsutella spp. in the North Central Region of the United States Soil Samples A total of 126 soil samples were collected from soybean fields or corn fields in South Dakota, Iowa, Michigan, Missouri, Wisconsin, and Kansas. The soil samples were stored at 4° C. for 2 to 5 months until used.

Examination of soil samples

Direct detection: Soil samples were examined directly without addition of bait J2. Native J2 were extracted from a 100-g subsample with a sucrose-flotation and centrifugation method. Total J2 and J2 parasitized by fungi were counted. Juveniles with attached fungal spore(s) or filled with mycelium were considered parasitized. To confirm parasitism of J2 by a fungus, three to five J2 with attached fungal spore(s) or filled with mycelium were handpicked from each infested soil sample and placed on potato dextrose agar. Fungi growing from the J2 were identified.

Baiting method: In this method, J2 were added into the soil one time to bait the fungal parasites. One hundred g soil from each sample were placed individually in a 240-ml plastic box (70×70×50 mm). About 2,000 newly hatched SCN J2 in 1 ml water were added to the surface of soil in each box. The boxes were covered with lids to reduce loss of soil moisture and to minimize contamination. They were maintained at room temperature (22-24° C.) under ambient light. After 14 days, J2 are be extracted, and percentage of J2 parasitized by the fungi was determined.

With the combination of the two detection methods, Hirsutella spp. colonization of J2 was observed in three soil samples (100%) from South Dakota, seven samples (47%) from Michigan, and nine samples (23%) from Iowa (Table 3). Hirsutella species were not observed in soil samples from, Missouri, Wisconsin and Kansas.

TABLE 3

Table 3. Frequency occurrence of Hirsutella spp. in soils collected from soybean fields in north central United States.

| State | Direct detection [a] | | Baiting[a] | | Total soil samples[b] | |
|---|---|---|---|---|---|---|
| | No. of samples examined | No. of samples with fungi | No. of samples examined | No. of samples with fungi | No. of samples examined | No. of samples with fungi |
| SD | 3 | 3 | 3 | 2 | 3 | 3 |
| IA | 38 | 0 | 38 | 9 | 38 | 9[c] |
| MI | 15 | 6 | 15 | 5 | 15 | 7 |
| MO | 42 | 0 | 42 | 0 | 42 | 0 |
| WI | 10 | 0 | 9 | 0 | 10 | 0 |
| KA | 18 | 0 | 17 | 0 | 18 | 0 |
| Total | 126 | 9 | 124 | 16 | 126 | 19 |
| % of samples with Hr spp. | | 7 | | 13 | | 15 |

[a]In direct detection, native second-stage juveniles (J2s) of Heterodera glycines were extracted from 100 g of soil and examined for parasitism by fungi. In baiting method, 2,000 J2s were added into 100 g of soil at day 0; the nematodes were recovered at day 14 and examined for parasitism by fungi.
[b]If the same soil sample was used in the two tests, it was counted one time. When Hr and/or Hm was observed in either test, the soil was considered positive for infestation.
[c]Fungal identities are to be confirmed.

EXAMPLE 3

Evaluation of Hirsutella Spp. as a Biocontrol Agent

*Hirsutella rhossiliensis* and *Hirsutella minnesotensis* are two major species of endoparasites of *Heterodera glycines* second-stage juveniles (J2). The objective of this study was to screen for the most effective isolates of the fungi in laboratory and greenhouse for biocontrol of the nematode. A total of 93 isolates of *H. rhossiliensis* and 25 isolates of *H. minnesotensis* were evaluated for parasitism of *H. glycines* J2 on cornmeal agar. Percentage of SCN J2 parasitized by the fungi varied among the fungal isolates. Most *H. rhossiliensis* isolates parasitized a high percentage of J2. The isolates of *H. rhossiliensis* obtained from bacteria-feeding nematodes, however, generally did not parasitize J2 on agar. *Hirsutella minnesotensis* parasitized lower percentage of J2 on agar than did *H. rhossiliensis.*

Forty isolates of *H. rhossiliensis* and four isolates of *H. minnesotensis* that parasitized a relatively high percentage of J2 as determined on agar were evaluated for their biocontrol potential in laboratory soil treated with microwave heating, which eliminates nematodes but does not kill most fungi and bacteria. Most isolates selected from the agar assay also parasitized a high percentage of J2 in the soil but there was variation among isolates. Correlation between the percentage of J2 parasitized on agar and percentage of J2 parasitized in soil was weak, suggesting environmental conditions are important in influencing parasitism. Pathogenicity of 14 isolates of *H. rhossiliensis* and four isolates of *H. minnesotensis* to the SCN was also investigated in the greenhouse suing untreated field soil. All isolates of *H. rhossiliensis* significantly reduced SCN density and increased plant growth when compared with non-inoculated soil control. Most isolates of *H. rhossiliensis* reduced SCN density and increased plant growth when compared with 1%-corn-grits control (culture media). One isolate (OWVT-1) of *H. rhossiliensis* reduced the SCN egg density by 95% and J2 density by 98% when compared with 1%-corn-grits control. Isolates of *H. minnesotensis,* however, neither reduced SCN density nor increased plant growth in the greenhouse. The nematode density in the greenhouse pots was negatively correlated with the percentage of J2 parasitized on agar ($R^2$=0.42, P<0.05) and laboratory pasteurized soil ($R^2$=0.47, P<0.05), indicating that the laboratory tests on agar and soil can only partially explain the control efficacy in the greenhouse natural soil. While laboratory tests on agar and in heat-treated soil permitted screening of potential isolates from a large number of isolates, the final step of screening isolates in the greenhouse using untreated field soil is necessary to find the most effective isolates as biological control agents (Liu and Chen, 2000b).

Fungal isolates and culture: The fungi were isolated from SCN J2 in soils collected from fields across southern Minnesota in 1997 and 1998 (Liu and Chen, 2000a). A few of the isolates were obtained from bacteria-feeding nematodes. The *H. rhossiliensis* isolate ATCC 46487 originally isolated from adult *Criconemella xenoplax* (Raski) Luc & Raski from soil in South Carolina (Jaffee & Zehr, 1985) was obtained from American Type Culture Collection. All isolates were maintained on potato dextrose agar (PDA) (Difco, Detroit, Mich.) at 48° C. The fungi were cultured on cornmeal agar (CMA) (Difco, Detroit, Mich.) for agar tests and for preparation of inoculum used in tests in soil in the laboratory and greenhouse. To prepare inoculum for the soil tests, the fungi were cultured on corn grits (Aunt Jemima, the Quaker Oats Company, Chicago, Ill.) at a ratio of 2:2:1 (sand:corn-grits:water) in 1-liter flasks for about 2 months at room temperature (22–25° C.). The number of colony forming units (cfu) per grain of corn grits was determined. Twenty grams of corn-grits culture per isolate plus 200 ml sterile distilled water were blended in a blender (model 57199, Hamilton beach/Proctor-Silex Inc.) 3 times, 10 seconds each time. A serial dilution of the fungal suspension was prepared. One ml of the suspension was placed onto the surface of a PDA plate. The number of colonies formed on agar were counted after 7 days.

Nematode: Soybean cyst nematode race 3 originally from a field in Minnesota was cultured on soybean C.V. Sturdy in sterilized soil in a greenhouse. Newly formed females and cysts were washed with a vigorously applied water stream through an 800-$\mu$m-aperture sieve onto a 250-$\mu$m-aperture and extracted by centrifugation in 76% (w/v) sucrose solution. Eggs were released from the cysts by breaking the cysts in a 40-ml glass tissue grinder (Fisher catalogue No. 08-414-

10D or equivalent). The eggs were separated from debris by centrifugation in 35% (w/v) sucrose solution for 5 minutes at 1,500 g and then transferred to an antibiotic solution of 100 μg/ml streptomycin sulfate, 50 μg/ml chlortetracycline and 20 μg/ml 8-quinilinol and maintained at 4° C. before being used. Before hatching, the eggs were rinsed with deionized water and transferred to a 4 mM $ZnCl_2$ solution. The nematodes were maintained at 22–25° C. and the J2 hatched within 2 days were collected. The J2 were rinsed with sterile deionized water and washed into a sterile beaker with 4.5 mM KCl before being used in the assays.

Soil: A field soil was collected from a corn field in Le Sueur County, Minnesota. *Hirsutella rhossiliensis* and *H. minnesotensis* was not observed on SCN J2 and other nematodes in the soil. Soil for the laboratory test was treated by microwave heating (1-kg lot of soil in a plastic bag for 1.5 min at 650 W), which eliminated nematodes, but allowed most fungi and bacteria to remain alive. The soil was air-dried, and passed through a 2-mm-aperture sieve. Soil moisture was adjusted to 7% (w/w). For the greenhouse test, the field soil was passed through a 5-mm-aperture sieve and was used without the heat treatment.

Test on agar: Ninety-three isolates of *H. rhossiliensis* (80 isolates isolated from SCN J2 and 13 isolates from bacteria-feeding nematodes) and 25 of *H. minnesotensis* (isolated from SCN J2) were tested for their ability to parasitize SCN J2 on agar. Discs 0.4-cm diameter were cut from the actively growing margin of a fungal colony growing on CMA, and one plug per isolate was transferred to the center of each of three 10-cm petri dishes containing CMA. The plates were sealed with parafilm and maintained at room temperature. After incubation for 5 weeks, approximately 300 SCN J2 in 0.1 ml of 4.5 mM KCl were added to the fungal culture in each petri dish. The dishes were uncovered for 30 minutes in a laminar flow cabinet to allow excess water to evaporate, then covered, and sealed with parafilm. At day 3, J2 were washed off using 5 ml 0.1% Tween-20 solution. The percentage of J2 colonized by the fungus or J2 with attached fungal spores was determined from 100 randomly selected J2 under an inverted microscope.

Laboratory test in soil: Forty isolates of *H. rhossiliensis* and four of *H. minnesotensis* that parasitized more than 50% J2 on agar (except the isolate FA2-1) were selected for evaluation in laboratory soil assay. Corn-grits cultures of *H.* rhossiliensis and *H. minnesotensis* were mixed separately with soil at a rate of 1% (corn grits:soil). A drain hole of 7 nun in diameter was made at the bottom of individual 25-ml vials with snap-on caps (Kerr Group Inc., Jackson, Tenn.) and a circle of polyester fabric was placed in the bottom to retain soil (McInnis and Jaffee, 1989). Twenty-five grams of soil were placed in each plastic vial, and five vials were used for each fungal isolate. After incubation for 3 weeks at room temperature (22–25° C.), 300 newly hatched J2 in 0.5 ml of 4.5 mM KCl were added onto the surface of the soil in each tube. After 3 days, the nematodes were recovered from the soil with a centrifugal-floatation technique (Jenkins, 1964). The percentage of J2 colonized by the fungus or J2 with attached fungal spores was determined from 50 randomly selected J2.

Greenhouse assay: Fourteen isolates of *H. rhossiliensis* and four isolates of *H. minnesotensis* that, except two isolates, parasitized more than 50% J2 in laboratory agar and soil assays were selected for this study. A corn-grits culture of each fungus was mixed separately with soil at a rate of 1%. Controls included the soil amended with 1% autoclaved corn-grits and the soil without addition of corn grits or fungal culture. Nematode eggs were added to the soil at a rate of 2,860 eggs/100 $cm^3$ soil at the same time. The soil was placed in 10-cm-diameter pots (300 ml). Seeds of soybean CV. Sturdy were surface-disinfected with 0.1% $NaOCl_3$ for 3 minutes and 2 seeds were sowed in each pot. After 1 week, the soybean plants were thinned to provide one plant per pot. Density of eggs, density of J2, and the percentage of J2 colonized by the fungus or with attached fungal spores were measured 2 months after inoculation. Plant heights and dry weights were determined. The nematode densities were expressed as number of eggs and number of J2 per 100 $cm^3$ soil or per gram of plant roots.

Data analysis: Data of egg and J2 densities were transformed to $\log_{10}(\chi)$ values and data of percentage of J2 parasitized by fungi were arcsine ($\chi$) transformed before being subjected to analysis of variance (ANOVA). Means were compared with the least significant difference test (LSD) at P=0.05. Contrast analyses were performed to compare the isolates of *H. rhossiliensis* with *H. minnesotensis* and compare the fungi with control. Regression analyses were performed to determine the relationship of fungal parasitism among the tests on agar, in laboratory soil, and in greenhouse, and to determine the relationship between fungal parasitism on water agar or laboratory soil and the nematode density in greenhouse pots treated with the fungi.

Parasitism on agar: Fungal isolates varied substantially in the proportion of SCN J2 infested (Table 4). About 69% of *H. rhossiliensis* isolates parasitized more than 50% J2 and 18% of isolates parasitized more than 80% of J2. The class of parasitism with the highest percentage frequency (28%) of *H. rhossiliensis* isolates was 71–80% J2 parasitized (Table 4). In contrast, only 16% of *H. minnesotensis* isolates parasitized more than 50% of J2. The class of parasitism with the highest percentage frequency (48%) of *H. minnesotensis* isolates was only 20–30% J2 parasitized (Table 4). None of the 13 isolates of *H. rhossiliensis* isolated from bacteria-feeding nematodes parasitized J2 within 3 days.

TABLE 4

Frequency distribution of isolates of *Hirsutella rhossiliensis* and *Hirsutella minnesotensis* among classes of percentage of second-stage juveniles (J2) of *Heterodera glycines* parasitized on agar and in laboratory soil.

| | on agar | | | | in soil | | | |
|---|---|---|---|---|---|---|---|---|
| | *H. rhossiliensis* | | *H. minnesotensis* | | *H. rhossiliensis* | | *H. minneasotensis* | |
| % J2 parasitized | No. of isolates | % Frequency | No. of isolates | % Frequency | No. of isolates | % Frequency | No. of isolates | % Frequency |
| 91–100% | 0 | 0 | 0 | 0 | 8 | 20.0 | 0 | 0 |
| 81–90% | 17 | 18.3 | 0 | 0 | 11 | 27.5 | 0 | 0 |

TABLE 4-continued

Frequency distribution of isolates of *Hirsutella rhossiliensis* and *Hirsutella minnesotensis* among classes of percentage of second-stage juveniles (J2) of *Heterodera glycines* parasitized on agar and in laboratory soil.

| | on agar | | | | in soil | | | |
|---|---|---|---|---|---|---|---|---|
| | *H. rhossiliensis* | | *H. minnesotensis* | | *H. rhossiliensis* | | *H. minneasotensis* | |
| % J2 parasitized | No. of isolates | % Frequency | No. of isolates | % Frequency | No. of isolates | % Frequency | No. of isolates | % Frequency |
| 71–80% | 26 | 28.0 | 0 | 0 | 7 | 17.5 | 2 | 50 |
| 61–70% | 12 | 12.9 | 2 | 8.0 | 2 | 5.0 | 1 | 25 |
| 51–60% | 9 | 9.7 | 2 | 8.0 | 5 | 12.5 | 0 | 0 |
| 41–50% | 5 | 5.4 | 0 | 0 | 1 | 2.5 | 1 | 25 |
| 31–40% | 5 | 5.4 | 4 | 16.0 | 1 | 2.5 | 0 | 0 |
| 21–30% | 4 | 4.3 | 12 | 48.0 | 1 | 2.5 | 0 | 0 |
| 11–20% | 1 | 1.1 | 5 | 20.0 | 0 | 0 | 0 | 0 |
| 1–10% | 1 | 1.1 | 0 | 0 | 3 | 7.5 | 0 | 0 |
| 0–1% | 13 | 14.0 | 0 | 0 | 1 | 2.5 | 0 | 0 |
| Total | 93 | | 25 | | 40 | | 4 | |

Parasitism in soil: Most fungal isolates that were highly effective in the agar assay were also able to parasitize a high proportion (more than 50%) SCN J2 in soil, though there were variations among isolates (Table 4). No significant relationship between the percentage of J2 parasitized on agar and the percentage of J2 parasitized in soil was observed ($R^2$=0.07, P=0.09). Among isolates that were subsequently used in the greenhouse assay, a positive relationship ($R^2$=0.28, P=0.03) between the percentage of J2 parasitized by the fungi on agar and percentage of J2 parasitized in the soil was observed. Some isolates parasitized a high percentage of J2 on agar but showed little or no ability to parasitize J2 in soil (Tables 4 and 5). Among the *H. minnesotensis* isolates, percentage of J2 parasitized by one isolate (FA2-1) was significantly lower than that of the other three isolates both on agar and in the soil test (Table 5).

TABLE 5

Percentage of second-stage juveniles (J2) of Heterodera glycines parasitized by Hirsutella rhossiliensis (Hr) and Hirsutella minnesotensis (Hm) in agar, laboratory soil, and greenhouse assays, and the colony-forming units (cfu) of the fungal culture for the laboratory and greenhouse soil sasays.

| Fungal species | Fungal isolate | Agar | Laboratory soil | Field soil in greenhouse | cfu ($10^5$) |
|---|---|---|---|---|---|
| Hr | WT24-1 | 87.8ab | 84.0def | 13.2fg | 67 |
| | ATCC | 88.7a | 72.8g | 22.8def | 49 |
| | WT4-1 | 86.4ab | 86.8cde | 33.6bcd | 71 |
| | MA37-1 | 87.4ab | 90.0bcd | 31.6bcde | 61 |
| | MA36.4-1 | 88.3ab | 82.0ef | 31.6bcde | 62 |
| | MA30-1 | 86.0ab | 92.0bc | 27.6bcde | 45 |
| | ST8-1 | 84.4abcd | 94.8ab | 37.6ab | 23 |
| | WA20-1 | 85.0abc | 35.2h | 38.0ab | 119 |
| | LE5.1-1 | 80.5bcde | ND | 19.6ef | ND |
| | WT8-1 | 83.9abcd | 96.8a | 23.2cdef | 70 |

TABLE 5-continued

Percentage of second-stage juveniles (J2) of Heterodera glycines parasitized by Hirsutella rhossiliensis (Hr) and Hirsutella minnesotensis (Hm) in agar, laboratory soil, and greenhouse assays, and the colony-forming units (cfu) of the fungal culture for the laboratory and greenhouse soil sasays.

| Fungal species | Fungal isolate | Agar | Laboratory soil | Field soil in greenhouse | cfu ($10^5$) |
|---|---|---|---|---|---|
| | FR6-1 | 75.8def | 87.6cde | 32.4bcd | 141 |
| | MO1-1 | 74.1ef | 83.2def | 23.2cdef | 44 |
| | JA9-1 | 77.6cdef | 96.0a | 28.8bcde | 67 |
| | OWVT-1 | 71.7fg | 91.6bc | 24.4cdef | 47 |
| Hm | WA23J2-1 | 61.3gh | 77.2fg | 49.2a | 22 |
| | RW7-1 | 63.1gh | 70.4g | 6.8g | 64 |
| | CRA3-2 | 51.4h | 68.0g | 35.2bcd | 7 |
| | FA2-1 | 17.51 | 43.2h | 36.0abc | 8 |
| Contrast | Hr vs. Hm | *** | *** | NS | |

Data of percentage of J2 parasitized are means of three, four, and five replicates on agar, laboratory soil, and greenhouse, respectively. Only the data of isolates used for the greenhouse test are included. The percentage values were transformed to arcsine ($\chi$) before being subjected to ANOVA. Means followed by different letters are significantly different at P=0.05 according to least significant difference test. *** and NS represent significant at P=0.001 and not significant at P=0.05, respectively. ND=not determined.

Biocontrol efficiency in greenhouse assay: All isolates of *H. rhossiliensis* tested in field soil significantly reduced the number of eggs and J2 developed per gram of plants when compared to the soil only control (Table 6).

TABLE 6

Density of *Heterodera glycines* eggs in pots treated with various isolates of *Hirsutella rhossiliensis* (*Hr*) and *Hirsutella minnesotensis* (*Hm*).

| Fungal species | Fungal isolate | Eggs/100 $cm^3$ of soil: Egg number | Eggs/100 $cm^3$ of soil: % Reduction compared with controls: Corn grits | Eggs/100 $cm^3$ of soil: % Reduction compared with controls: Soil only | Eggs/gram of plant: Egg number | Eggs/gram of plant: % Reduction compared with controls: Corn grits | Eggs/gram of plant: % Reduction compared with controls: Soil only |
|---|---|---|---|---|---|---|---|
| *Hr* | ATCC46487 | 66,920bcde | 11.5 | 16.4 | 87,630defg | 35.3 | 88.7 |
| | OWVT-1 | 1,907h | 97.5 | 97.6 | 3,430j | 97.5 | 99.6 |
| | MO1-1 | 30,063g | 60.2 | 62.4 | 32,428i | 76.1 | 95.8 |
| | FR6-1 | 28,860fg | 61.8 | 63.9 | 30,891i | 77.2 | 96.0 |
| | JA9-1 | 40,087efg | 47.0 | 49.9 | 46,783hi | 65.5 | 94.0 |
| | LE5.1-1 | 36,800defg | 51.3 | 54.0 | 36,301hi | 73.2 | 95.3 |
| | WT8-1 | 33,500efg | 55.7 | 58.2 | 36,667i | 72.9 | 95.3 |
| | MA36.4-1 | 37,960cdefg | 49.8 | 52.6 | 50,335fghi | 62.8 | 93.5 |
| | ST8-1 | 29,840fg | 60.5 | 62.7 | 33,318i | 75.4 | 95.7 |
| | WA20-1 | 77,560abcd | −2.6 | 3.1 | 110,493cdef | 18.4 | 85.8 |
| | MA30-1 | 32,880fg | 56.5 | 58.9 | 42,051hi | 69.0 | 94.6 |
| | WT4-1 | 88,240abc | −16.7 | −10.2 | 89,275cdefg | 34.1 | 88.5 |
| | MA37-1 | 38,280cdefg | 49.4 | 52.2 | 43,214ghi | 68.1 | 94.4 |
| | WT24-1 | 56,900bcdef | 24.7 | 28.9 | 81,901efgh | 39.5 | 89.5 |
| *Hm* | FA2-1 | 119,200ab | −57.7 | −48.9 | 226,357b | −67.1 | 70.9 |
| | CRA3-2 | 112,120ab | −48.3 | −40.1 | 199,129bc | −47.0 | 74.4 |
| | RW7-1 | 135,000a | −78.6 | −68.6 | 285,545b | −110.8 | 63.3 |
| | WA23J2-1 | 112,700ab | −49.1 | −40.8 | 175,307bcd | −29.4 | 77.5 |
| Controls | 1% corn grits | 75,600abcd | | 5.6 | 135,436bcde | | 82.6 |
| | Soil only | 80,050abcd | −5.9 | | 778,250a | −474.6 | |
| Contrast | *Hr* vs. Control | *** | | | *** | | |
| | *Hm* vs. Control | * | | | NS | | |
| | *Hr* vs. *Hm* | *** | | | *** | | |

Data are means of five replicates. The values were transformed to $\log_{10}$ ($\chi$) values before being subjected to ANOVA. Means followed by different letters are significantly different at P=0.05 according to least significant difference test. * and *** represent significant at P=0.05 and P=0.001, respectively. NS means not significant at P=0.05.

Seventy-one percent (ten of the 14) isolates of *H. rhossiliensis* significantly reduced the number of SCN eggs and 43% (six of 14) isolates significantly reduced number of J2 per gram of plants when compared with the 1%-corn-grits control (Tables 6 and 7). Fifty percent (seven of 14) isolates of *H. rhossiliensis* reduced the number of eggs per 100 $cm^3$ of soil when compared with the soil only control or 1%-corn-grits control. Only twenty-one percent (three of the 14) isolates of *H. rhossiliensis* significantly reduced the number of J2 per 100 $cm^3$ of soil when compared with the soil only control and two isolates when compared with the 1%-corn-grits control. Egg and J2 densities were lowest in pots inoculated with *H. rhossiliensis* OWVT-1. This fungal isolate reduced the number of eggs per gram of plant by 95% and number of J2 per gram of plant by 98% when compared with the 1%-corn-grits control. None of isolates of *H. minnesotensis,* however, reduced egg and J2 densities in soil or on plants (Tables 6 and 7).

TABLE 7

Density of *Heterodera glycines* second-stage juvenile (J2) in pots treated with various isolates of *Hirsutella rhossiliensis* (*Hr*) and *Hirsutella minnesotensis* (*Hm*).

| Fungal species | Fungal isolate | J2 density per 100 $cm^3$ of soil: J2 number | J2 density per 100 $cm^3$ of soil: % Reduction compared with controls: Corn grits | J2 density per 100 $cm^3$ of soil: % Reduction compared with controls: Soil only | J2/gram of plant: J2 number | J2/gram of plant: % Reduction compared with controls: Corn grits | J2/gram of plant: % Reduction compared with controls: Soil only |
|---|---|---|---|---|---|---|---|
| *Hr* | ATCC46487 | 7,532bcde | −47.5 | −39.3 | 9,704defgh | −5.6 | 82.1 |
| | OWVT-1 | 268h | 94.8 | 95.1 | 4811 | 94.8 | 99.1 |

TABLE 7-continued

Density of *Heterodera glycines* second-stage juvenile (J2) in pots treated with various isolates of *Hirsutella rhossiliensis* (*Hr*) and *Hirsutella minnesotensis* (*Hm*).

| Fungal species | Fungal isolate | J2 density per 100 $cm^3$ of soil: J2 number | % Reduction compared with controls: Corn grits | % Reduction compared with controls: Soil only | J2/gram of plant: J2 number | % Reduction compared with controls: Corn grits | % Reduction compared with controls: Soil only |
|---|---|---|---|---|---|---|---|
| | MO1-1 | 2,700defg | 47.1 | 50.1 | 2,910ghijk | 68.3 | 94.6 |
| | FR6-1 | 1,478g | 71.1 | 72.7 | 1,579k | 82.8 | 97.1 |
| | JA9-1 | 4,133efg | 19.1 | 23.6 | 4,634ijk | 49.6 | 91.4 |
| | LE5.1-1 | 3,106defg | 39.2 | 42.6 | 3,069hijk | 66.6 | 94.3 |
| | WT8-1 | 3,511defg | 31.3 | 35.1 | 3,886fghijk | 57.7 | 92.8 |
| | MA36.4-1 | 2,534defg | 50.4 | 53.1 | 3,353fghij | 63.5 | 93.8 |
| | ST8-1 | 2,045fg | 60.0 | 62.2 | 2,278jk | 75.2 | 95.8 |
| | WA20-1 | 6,432abcd | −25.9 | −18.9 | 8,884cdef | 3.3 | 83.6 |
| | MA30-1 | 2,428efg | 52.5 | 55.1 | 3,173ghijk | 65.5 | 94.1 |
| | WT4-1 | 5,768cdef | −12.9 | −6.7 | 5,520fghij | 39.9 | 89.8 |
| | MA37-1 | 2,382defg | 53.4 | 56.0 | 2,684hijk | 70.8 | 95.0 |
| | WT24-1 | 4,356cdef | 14.7 | 19.5 | 6,103efghi | 33.6 | 88.7 |
| *Hm* | FA2-1 | 18764a | −267.3 | −247.0 | 36,066ab | −292.4 | 33.5 |
| | CRA3-2 | 7816abc | −53.0 | −44.5 | 14,064bcde | −53.0 | 74.1 |
| | RW7-1 | 8480abc | −66.0 | −56.8 | 17,479bcd | −90.2 | 67.8 |
| | WA23J2-1 | 13072ab | −155.9 | −141.7 | 20,076abc | −118.4 | 63.0 |
| Controls | 1% corn grits | 5,108cdef | | 5.5 | 9,192defg | | 83.0 |
| | Soil only | 5,408cde | −5.9 | | 54,200a | −489.6 | |
| Contrast | *Hr* vs. Control | * | | | *** | | |
| | *Hm* vs. Control | ** | | | NS | | |
| | *Hr* vs. *Hm* | *** | | | *** | | |

Data are means of five replicates. J2 densities were transformed to $\log_{10}$ ($\chi$) values before being subjected to ANOVA. Means followed by different letters are significantly different at P=0.05 according to least significant difference test. *, , * represent significant at P=0.05, P=0.01, and P=0.001, respectively. NS means not significant at P=0.05.

No parasitism of J2 by Hirsutella species in the soil of either control was observed. In contrast, in soil inoculated with Hirsutella spp., between 20% to 50% of J2 were parasitized at the end of the test (Table 7). The percentage of J2 parasitized at the end of the test in field soil in the greenhouse was not correlated with the percentage of J2 parasitized on agar or in laboratory soil.

The number of eggs per gram of plant in the greenhouse pots was negatively related to percentage of J2 parasitized on agar ($R^2$=0.42, P=0.0035) and laboratory soil ($R^2$=0.47, P=0.0025) (FIG. 1). A similar relationship was observed between the fungal parasitism of J2 on agar or laboratory soil and number of eggs per 100 $cm^3$ soil, number of J2 per 100 $cm^3$ soil or per gram of plant (data not shown). No significant relationship between egg density and percentage of J2 parasitized in the pots at the end of the experiment was observed (data not shown).

Ninety-three percent (13 of 14) *H. rhossiliensis* isolates significantly (P<0.05) increased plant weights and 14% (two of 14) isolates significantly (P<0.05) increased plant heights compared with the 1%-corn-grits control (Table 8). However, no difference in plant growth was observed among plants in *H. minnesotensis* inoculated soil and the 1%-corn-grits control. The plant heights and weights were lower (P<0.5) in pots of soil only control than any other treatments including the control of 1% corn grits (Table 8).

TABLE 8

Growth of soybean plants in pots infested with *Heterodera glycines* and treated with various isolates of *Hirsutella rhossiliensis* (*Hr*) and *Hirsutella minnesotensis* (*Hm*).

| Fungal Species | Fungal isolate | Plant weight Grams/pot | Plant weight % Increase compared with controls Corn grits | Plant weight % Increase compared with controls Soil only | Plant height cm | Plant height % Increase compared with controls Corn grits | Plant height % Increase compared with controls Soil only |
|---|---|---|---|---|---|---|---|
| *Hr* | ATCC46487 | 2.2def | 38.3 | 559 | 68.6efg | −6.8 | 43.5 |
| | OWVT-1 | 1.5fghi | 12.3 | 435 | 83.0abc | 12.8 | 73.6 |
| | MO1-1 | 2.8ab | 72.8 | 724 | 78.8abcdef | 7.1 | 64.9 |
| | FR6-1 | 2.8ab | 75.3 | 735 | 81.2abcde | 10.3 | 69.9 |
| | JA9-1 | 2.6bcd | 59.3 | 659 | 90.4a | 22.8 | 89.1 |
| | LE5.1-1 | 3.0a | 86.4 | 788 | 83.8abc | 13.9 | 75.3 |
| | WT8-1 | 2.7abc | 66.7 | 694 | 87.0ab | 18.2 | 82.0 |
| | MA36.4-1 | 2.3cde | 40.7 | 571 | 74.2bcdefg | 0.8 | 55.2 |
| | ST8-1 | 2.5bcd | 55.6 | 641 | 76.4bcdefg | 3.8 | 59.8 |
| | WA20-1 | 2.2def | 37.0 | 553 | 82.0abcd | 11.4 | 71.5 |
| | MA30-1 | 2.2defg | 35.8 | 547 | 78.6abcdefg | 6.8 | 64.4 |
| | WT4-1 | 2.9ab | 76.5 | 741 | 86.4abc | 17.4 | 80.8 |
| | MA37-1 | 2.6abcd | 61.7 | 671 | 85.4abc | 16.0 | 78.7 |
| | WT24-1 | 2.2defg | 35.8 | 547 | 77.0bcdefg | 4.6 | 61.1 |
| *Hm* | FA2-1 | 1.6hi | 0 | 433 | 69.4defg | −5.7 | 45.2 |
| | CRA3-2 | 1.8ghi | 11.3 | 493 | 82.8abc | 12.5 | 73.2 |
| | RW7-1 | 1.5i | −5.0 | 407 | 65.4g | −11.1 | 36.8 |
| | WA23J2-1 | 2.0efgh | 26.3 | 573 | 67.0fg | −9.0 | 40.2 |
| Controls | 1% corn grits | 1.6hi | | 376 | 73.6cdefg | | 54.0 |
| | Soil only | 0.3j | −79.0 | | 47.8h | −35.1 | |
| Contrast | *Hr* vs. Control | *** | | | *** | | |
| | *Hm* vs. Control | *** | | | * | | |
| | *Hr* vs. *Hm* | *** | | | *** | | |

Data are means of five replicates. Means followed by different letters are significantly different at P=0.05 according to least significant difference test. * and *** represent significant at P=0.05 and P=0.001, respectively.

The density of SCN generally is expressed as number of eggs per 100 $cm^3$ of soil. However, reproduction is dependent on available food source, i.e., more soybean roots support more nematode reproduction. In the present greenhouse test, soybean plants in the soil-only control grew poorly and their plant mass was significantly less than in other treatments. Thus, to minimize bias in the present analysis of nematode population density, the number of eggs or J2 per gram of plant were used as well as the number of eggs or J2 per 100 $cm^3$ of soil.

The present results indicate that host specificity exists among isolates of *H. rhossiliensis* and *H. minnesotensis*. Isolates from bacteria-feeding nematodes did not infect SCN J2 within 3 days. Previous studies demonstrated that *H. rhossiliensis* and/or *H. minnesotensis* were isolated from only one species of host in one field (Jaffee et al., 1991; Liu and Chen, 2000a). Tedford et al. (1994) divided 25 isolates of *H. rhossiliensis* into four groups according to their hosts. The isolates from *R. robustus* and *H. galeatus* grew slowly in culture, but actively sporulated, produced larger conidia, and were weakly parasitic to *H. schachtii, M. javanica,* and *S. glaseri*.

The methodology applied in the present agar tests and in laboratory soil might have some limitations that reduced the chances to identify highly effective biocontrol agents. First, the ratio of spores on agar or in soil compared to inoculated nematode numbers is too high. In the agar and in soil tests, one nematode probably encountered over 1,000 spores. Consequently, the percentage of J2 parasitized may not differentiate among isolates. Second, only the percentage of parasitized J2 was measured after 3 days. Greater biological and ecological differences might be detected if more characteristics, such as optimum temperature, soil moisture, growth rate and sporulation, were measured. Finally, many factors, such as culture media, time and temperature of incubation, and assay substrate, affect parasitism. For example, Dickie and Bell (1995) examined the effect of nine factors on the outcome of classic in vitro screens testing the antagonistic action of endophytic bacterial isolates from grape vines against virulent *Agobacterium vitis,* and found that nine factors had a significant effect on the diameter of the inhibition zones. For these reasons the in vitro screening system for nematophagous fungi could be improved.

The negative relationship between nematode density in soil in greenhouse pots and percentage of J2 parasitized on agar and in laboratory soil suggests that the agar and laboratory soil assays can only partially explain the control efficacy in the greenhouse natural soil. While laboratory tests on agar and in soil enable one to screen a large number of isolates, the step of screening isolates in field soil in the greenhouse is still necessary to find the most effective isolates as biological control agents.

The present inventors found that one isolate (OWVT-1) of *H. rhossiliensis* was highly effective in suppressing SCN density in the natural soil under greenhouse conditions. The fungus was isolated from a site where soybean has been continuously planted for 27 years and the nematode density was naturally suppressed (Chen, 1997). The long-term monoculture of soybean may select for fungi having high level of pathogenicity to the nematode. The present greenhouse assay enabled the inventors to detect the highly pathogenic fungus in natural soil.

EXAMPLE 4

Determination of Spore Production, Infectivity Saprophytic Activity, Transmission, and Mortality of *H. minnesotensis.*

Spore production: Three isolates, representing relatively high, moderate, and low pathogenicity to SCN, are used in the present study. Ten agar disks (1-cm diameter) are removed with a cork borer from plastic petri dishes (10-cm diameter) containing water agar. One fungus-colonized J2 is placed in a small drop of distilled water on the surface of plastic in each of the 10 circular areas where agar is removed. The dish is sealed with parafilm and maintained at 25° C., and each nematode is examined daily for spore production. Ten replicates (10 petri dishes) are used for each isolate.

Spore infectivity: Detached spores of *H. rhossiliensis,* a species similar to *H. minnesotensis,* cannot attach to host nematode and lose infectivity. This experiment is designed to determine the infectivity of *H. minnesotensis* spores detached from phialides. A highly pathogenic isolate is cultured on corn grits. Detached spores are collected. The following three methods are used: (i) 100 J2 are mixed with 1,000, 10,000, and 100,000 spores in 1.5 ml of soil extract solution in a microfuge tube and centrifuged at 10,000 g for 5, 10, or 20 minutes. (ii) 10,000 spores in 1 ml of sterile soil extract solution are placed on water agar in a petri dish and 100 J2 are added. The plates are incubated at 25° C. for 24 hours. (iii) 100,000 spores are mixed with 25 grams of sterile soil and 300 J2 are added on the top of soil. After 2 days of incubation at 25° C., the J2 are recovered from the soil. The J2 treated with the three methods are examined for spores attached to nematode cuticle.

Saprophytic growth and spore production in soil: Spore suspension is prepared. In addition, mycelium suspension without spores is prepared. The fungal colony forming units (cfu) are determined. Soil collected from a field without SCN and *H. minnesotensis* is autoclaved, treated with microwave heating (1-kg lot for 1.5 minutes at 650 W to kill microscopic animals but keep fungal and bacterial populations), or used without heating treatment. About 10,000 cfu of fungal suspension are mixed with 25 grams of soil and placed in vials. At days 0, 3, 7, 14, 21, and 28, five vials of each combination of fungal suspension and soil are assayed for spore production by adding 300 J2 on surface of the soil in each vial. J2 are recovered from the soil after 3 days and number of spores attached to J2 are determined.

Spore transmission: Soil without SCN and *H. minnesotensis* is collected from a field and treated with microwave heating. A highly pathogenic isolate is used in this study. The fungus is cultured on corn grits. The fungal culture is mixed with sterile soil at 1:10, placed in 10-cm-diameter petri dishes, and incubated for 1 week before adding SCN J2 (5,000 J2/dish). After 3 days, the nematodes are recovered and percent of J2 attached with spores and percent of J2 colonized by the fungus is determined. Fungus-colonized J2 (0, 1, 3, 9, 27, 81, 243, and 729 J2/vial) are mixed with 25 grams of soil that is placed in vials. After 1 to 2 weeks, 300 healthy J2 are added on the top of soil in each vial. The nematodes are recovered from the soil after 3 days and examined for fungal spore attachment. The probability of spore acquisition is determined.

Spore mortality: The design of this experiment is based on the assumption that the fungus cannot grow saprophytically and cannot produce spores without nematodes as substrate in soil. The fungus-colonized J2 are prepared and added into vials containing natural field soil. Fungus-colonized J2 are added at a level that is needed for about 90% J2 transmission. At days 10, 20, 30, 60, 90, 120, 150, 210, 270, and 330, five vials are assayed to determine spore transmission.

EXAMPLE 5

Determination of Host Range of *H. minnesotensis*

Host range is an important character in population dynamics and epidemics of a pathogen and the information is important for development of the fungus as a biocontrol agent. Three isolates of *H. minnesotensis* and one isolate of *H. thompsonii* var. *thompsonii,* which is a parasite of mites and closely related to *H. minnesotensis* morphologically, is tested on nematodes, insects, and mites.

A. Nematode hosts: Nematodes used in this experiment included plant-parasitic nematodes *Heterodera glycines, Meloidogyne incognita, Meloidogyne hapla, Meloidogyne javanica, Meloidogyne arenaria,* Hoplolaimus sp., and Scutellonema sp.; insect-parasitic nematodes *Stinernema glaseri* and *Heterorhabditis bacteriophora;* and fungal-feeding nematodes Aphelenchus sp. and Aphelenchoides sp. The fungi were cultured on CMA and the nematodes are exposed to the fungal culture for 3 days. Percentages of nematodes attached by spores or filled with mycelium are recorded. The J2 were then transferred onto water agar to determine colonization of J2 by the fungus. All nematodes tested were hosts of the fungus. Percentage of J2 with attached spores or filled with mycelium after 3 days of exposure to the fungal culture are summarized in Table 9.

TABLE 9

Percentage of nematodes parasitized by *Hirsutella minnesotensis* after 3 days on CMA culture.

| Nematode | FA2-1 | MA13-1 | WA23-1 |
|---|---|---|---|
| Aphelenchoides sp. | 31.8 | 54.9 | 37.3 |
| Aphelenchus sp. | 25.2 | 32.5 | 43.6 |
| *Heterodera glycines* | 11.8 | 17.7 | 21.1 |
| *Heterorhabditis bacteriophora* | — | — | 1.1 |
| Hoplolaimus sp. | 100 | 100 | — |
| *Meloidogyne arenaria* | 50.0 | 58.7 | 58.3 |
| *Meloidogyne hapla* | 6.9 | 36.6 | 20.8 |
| *Meloidogyne incognica* | 31.3 | 22.8 | 29.1 |
| *Meloidogyne javanica* | 20.0 | 21.8 | 16.7 |
| Scutellonema sp. | 11.4 | 18.6 | 24.4 |
| *Stinernema glaseri* | 3.4 | 14.0 | 4.8 |

B. Insect hosts: Insect species common in Minnesota, at least including corn root worm, European corn borer and corn ear worm, and one to two species of soil mites are tested. Because the mode of infection is unknown if any of the species is a host of *H. minnesotensis,* three methods are used for the study.

(i) Twenty insects and 100 mites of each species are added separately onto the fungal culture on CMA, and infection and mortality are examined daily. The insects and mites on CMA without fungal culture serve as control.

(ii) Spore and mycelium suspension in water are prepared from culture on corn grits. The insects and mites are maintained separately on artificial media or on plants, and sprayed with fungal spore and mycelium suspension. Treatment with water is included as control. Infection and mortality are examined daily.

(iii) The fungus is cultured on corn grits, and mixed with autoclaved soil at 1:10. One hundred $cm^3$ of the mixture is placed in a 250-ml beaker and covered with foil. After 1 week, 20 insects and 500 mites are introduced separately into the soil in each beaker. Autoclaved soil mixed with autoclaved fungal culture are included as control. The insects and mites are extracted from the soil at days 3, 5, and 7, and their infection by the fungus and mortality are examined.

EXAMPLE 6

Evaluation of Biological Control Efficacy of *H. minnesotensis* and *H. rhossiliensis* Against SCN in Fields 1998 Field Trial A field experiment was conducted at one site in Waseca in 1998. Fungi used in this study included three species of egg-parasitic fungi, *Verticillium chlamydosporium* from Florida, ARF18 from Arkansas, and *Cylindrocarpon destructans* from Minnesota, and two species of juvenile-parasitic fungi, *Hirsutella rhossiliensis* and *Hirsutella minnesotensis* from Minnesota. The fungi were cultured on corn-grits, applied in furrow and mixed into soil. Additionally, aldicarb (nematicide) and lorsban (insecticide) were included for a comparison purpose. Plots applied with fungal culture medium, without addition of the culture medium, and plots with a resistant cultivar Pioneer 9234 were included as controls. Each plot consisted of two rows with row spacing of 30 inches and row length of 15 feet. The plots were separated by four rows without application of agents. Four replicates were used. Nematode egg density at planting, and egg density and juvenile density 2 months after planting and at harvest were determined. Soybean yield was recorded. Levels of fungal parasitism of nematode eggs and juveniles were measured 2 months after planting and at harvest.

The nematode population response to the fungal and nematicidal treatment was summarized in Table 10. Resistant cultivar Pioneer 9234 was the most effective in reducing the nematode population density (96% reduction). The nematicide aldicarb reduced 64% of eggs and 66% of J2 at the end of season compared to average of the three controls. There was no reduction of the nematode density in plots treated with the egg-parasitic fungi, *Verticillium chlamydosporium, Cylindrocarpon destructans,* and ARF18. However, the J2-parasitic fungi, *H. minnesotensis* and *H. rhossiliensis,* significantly reduced the nematode population density. When they were applied alone, *H. minnesotensis* at dosage of 0.5% reduced 58% of eggs and 56% of J2 at the end of the season. *Hirsutella minnesotensis* at dosage of 0.1% was also effective in control of the nematode with 45% egg reduction and 62% J2 reduction at the end of season. *Hirsutella rhossiliensis* reduced egg density by 32% and J2 density by 31% at the end of the season. When the Hirsutella species applied with the egg-parasitic fungi, the control efficacy was reduced, suggesting that the egg-parasitic fungi had antagonistic effect on the J2-parasitic fungi.

TABLE 10

Population development of the soybean cyst nematode in field plots treated with nematophagous fungi and nematicides in 1998.

| | | Egg population | | | | | | | |
|---|---|---|---|---|---|---|---|---|---|
| | | At planting | Midseason | | End season | | | | |
| | | Eggs/100 | Eggs/100 | % | Eggs/100 | % | Reproduction rate[b] | | |
| Agent | Dosage | $cm^3$ soil | $cm^3$ soil | Reduction[a] | $cm^3$ soil | Reduction[a] | Pf/Pi | Pf/Pm | Pm/Pi |
| *Verticillium chlamydosporium* (*V. c.*) | 0.5% | 1,588 | 2,669 | 7 | 18,363 | −38 | 19.1 | 6.9 | 3.3 |
| *Cylindrocarpon destructans* | 0.5% | 1,285 | 3,825 | −34 | 13,450 | −1 | 10.5 | 3.6 | 2.9 |
| ARF 18 | 0.5% | 1,372 | 3,994 | −40 | 16,750 | −26 | 13.6 | 4.5 | 3.1 |
| *Hirsutella rhossiliensis* (*H. r.*) | 0.5% | 966 | 2,206 | 23 | 9,125 | 32 | 10.2 | 5.6 | 2.2 |
| Hirsutella sp. (H. sp.) | 0.5% | 757 | 2,256 | 21 | 5,566 | 58 | 7.7 | 3.2 | 2.8 |
| *V. c.* | 0.1% | 1,238 | 3,825 | −34 | 14,763 | −11 | 15.4 | 4.8 | 3.3 |
| H. sp. | 0.1% | 1,285 | 2,625 | 8 | 7,313 | 45 | 6.4 | 3.4 | 2.1 |
| *V. c.* + *H. r.* | 0.5% + 0.5% | 557 | 2,519 | 12 | 10,725 | 20 | 24.7 | 5.1 | 4.8 |
| *V. c* + H. sp. | 0.5% + 0.5% | 1,066 | 3,200 | −12 | 13,688 | −3 | 14.7 | 5.2 | 3.7 |
| CM60 | Seed-coating | 1,610 | 4,306 | −50 | 15,450 | −16 | 14.4 | 3.7 | 3.9 |
| *V. c.* + *H. r.* + CM60 | 0.5% + 0.5% | 650 | 2,013 | 30 | 13,963 | −5 | 26.2 | 8.9 | 3.1 |
| *V. c.* + H. sp. + CM60 | 0.5% + 0.5% | 1,297 | 3,481 | −22 | 9,050 | 32 | 7.7 | 2.9 | 3.0 |
| Aldicarb | 1200 g ai/acre | 772 | 1,200 | 58 | 4,788 | 64 | 6.5 | 4.5 | 1.6 |
| Lorsban | 1800 g ai/acre | 785 | 3,525 | −23 | 13,588 | −2 | 19.0 | 6.0 | 4.9 |
| Resistant cultivar Pioneer 9234 | | 1,222 | 838 | 71 | 472 | 96 | 0.5 | 0.6 | 0.7 |
| Control 1 - with autoclaved carrier | 0.5% | 1,050 | 2,719 | 5 | 12,500 | 6 | 13.9 | 5.4 | 2.6 |
| Control 2 - with autoclaved carrier | 1% | 1,160 | 1,994 | 30 | 14,725 | −10 | 16.7 | 9.0 | 2.2 |
| Control 3 - without agent | | 1,013 | 3,875 | −35 | 12,813 | 4 | 15.9 | 3.9 | 4.8 |
| Average of the three controls | | 1074.2 | 2862.5 | | 13345.8 | | 15.5 | 6.1 | 3.2 |

TABLE 10-continued

Population development of the soybean cyst nematode in field plots treated with nematophagous fungi and nematicides in 1998.

| | | Juvenile (J2) population | | | |
|---|---|---|---|---|---|
| | | Midseason | | End season | |
| Agent | Dosage | J2/100 $cm^3$ soil | % Reduction[a] | J2/100 $cm^3$ soil | Reduction[a] |
| *Verticillium chlamydosporium* (*V. c.*) | 0.5% | 254 | 8 | 255 | 13 |
| *Cylindrocarpon destructans* | 0.5% | 211 | 24 | 262 | 11 |
| ARF 18 | 0.5% | 268 | 3 | 360 | −23 |
| *Hirsutella rhossiliensis* (*H. r.*) | 0.5% | 145 | 48 | 202 | 31 |
| Hirsutella sp. (H. sp.) | 0.5% | 210 | 24 | 128 | 56 |
| *V. c.* | 0.1% | 468 | −69 | 305 | −4 |
| H. sp. | 0.1% | 198 | 29 | 112 | 62 |
| *V. c.* + *H. r.* | 0.5% + 0.5% | 250 | 10 | 209 | 29 |
| *V. c* + H. sp. | 0.5% + 0.5% | 98 | 65 | 176 | 40 |
| CM60 | Seed-coating | 277 | 0 | 215 | 27 |
| *V. c.* + *H. r.* + CM60 | 0.5% + 0.5% | 139 | 50 | 228 | 22 |
| *V. c.* + H. sp. + CM60 | 0.5% + 0.5% | 191 | 31 | 208 | 29 |
| Aldicarb | 1200 g ai/acre | 129 | 54 | 98 | 66 |
| Lorsban | 1800 g ai/acre | 434 | −57 | 186 | 37 |
| Resistant cultivar Pioneer 9234 | | 45 | 84 | 11 | 96 |
| Control 1 - with autoclaved carrier | 0.5% | 355 | | 318 | |
| Control 2 - with autoclaved carrier | 1% | 173 | | 307 | |
| Control 3 - without agent | | 304 | | 254 | |
| Average of the three controls | | 277 | | 293 | |

[a]compared with the average of three controls.
[b]Pi = eggs/100 $cm^3$ soil at planting; Pm = eggs/100 $cm^3$ soil at midseason, and Pf = eggs/100 $cm^3$ soil at the end season.

Observed percentage of J2 parasitized by the fungi was low. At midseason, only in plots treated with *H. minnesotensis* more then 10% of J2 were parasitized. Parasitism of J2 by fungi was generally not observed at midseason in plots without addition of the Hirsutella species. At the end of season, parasitism of J2 was detected in all treatments except the plots planted with the resistant cultivar Pioneer 9234, in which the J2 density was low (Table 11).

TABLE 11

Fungal parasitism of second-stage juveniles (J2) of the soybean cyst nematode in field plots treated with nematophagous fungi and nematicides in 1998.

| | | % J2 parasitized | |
|---|---|---|---|
| Agent | Dosage | Midseason | End season |
| *Verticillium chlamydosporium* (*V.c.*) | 0.5% | 0 | 11 |
| *Cylindrocarpon destructans* | 0.5% | 2 | 2 |
| ARF 18 | 0.5% | 0 | 14 |
| *Hirsutella rhossiliensis* (*H.r.*) | 0.5% | 3 | 12 |
| Hirsutella sp. (H.sp.) | 0.5% | 10 | 10 |
| *V.c.* | 0.1% | 0 | 3 |
| H. sp. | 0.1% | 18 | 4 |
| *V.c.* + *H.r.* | 0.5% + 0.5% | 0 | 22 |
| *V.c.* + H.sp. | 0.5% + 0.5% | 3 | 14 |
| CM60 | Seed-coating | 0 | 4 |
| *V.c.* + *H.r.* + CM60 | 0.5% + 0.5% | 3 | 13 |
| *V.c.* + H.sp. + CM60 | 0.5% + 0.5% | 4 | 10 |
| Aldicarb | 1200 g ai/acre | 0 | 4 |
| Lorsban | 1800 g ai/acre | 0 | 16 |
| Resistant cultivar Pioneer 9234 | | 0 | 0 |
| Control 1 - with autoclaved carrier | 0.5% | 0 | 7 |
| Control 2 - with autoclaved carrier | 1% | 0 | 5 |
| Control 3 - without agent | | 1 | 4 |

There was no statistically significant difference of plant growth (stand and soybean yield) among the treatments (Table 12). Emergence rate was the highest in the control plots without addition of agent and the plots planted with Pioneer 9234. In the plots treated with a combination of *V. chlamydosporium, H. rhossiliensis,* and the soybean root-growth-promoting agent CM60, the emergence rate was only 68%. The difference of emergence was probably attributed to the variations of seeding depth rather the effect of the agents.

TABLE 12

Soybean plant growth in field plots infested with the soybean cyst nematode and treated with nematophagous fungi and nematicides in 1998.

| Agent | Dosage | Plant growth: Emergence rate (%) | Plant growth: Yield (Bul/Acre) |
|---|---|---|---|
| *Verticillium chlamydosporium* (*V.c.*) | 0.5% | 88.4 | 20.7 |
| *Cylindrocarpon destructans* | 0.5% | 89.1 | 17.1 |
| ARF 18 | 0.5% | 89.1 | 23.5 |
| *Hirsutella rhossiliensis* (*H.r.*) | 0.5% | 84.1 | 25.6 |
| Hirsutella sp. (H.sp.) | 0.5% | 88.2 | 23.9 |
| *V.c.* | 0.1% | 87.9 | 20.3 |
| H. sp. | 0.1% | 91.9 | 19.7 |
| *V. c.* + *H.r.* | 0.5% + 0.5% | 83.6 | 27.1 |
| *V.c* + H.sp. | 0.5% + 0.5% | 88.1 | 23.0 |
| CM60 | Seed-coating | 87.7 | 19.5 |
| *V.c.* + *H.r.* + CM60 | 0.5% + 0.5% | 68.1 | 24.4 |
| *V.c.* + H.sp. + CM60 | 0.5% + 0.5% | 80.9 | 22.6 |
| Aldicarb | 1200 g ai/acre | 88.4 | 23.0 |
| Lorsban | 1800 g ai/acre | 80.3 | 26.0 |
| Resistant cultivar Pioneer 9234 | | 93.1 | 27.2 |
| Control 1 - with autoclaved carrier | 0.5% | 88.9 | 22.3 |
| Control 2 - with autoclaved carrier | 1% | 86.0 | 19.9 |
| Control 3 - without agent | | 93.1 | 24.4 |
| Average of the three controls | | 89.3 | 22.2 |

1999 Field Trails

The methodology applied in 1999 was the same as used in 1998 except a few fungal agents were different and fungal parasitism was only measured in the Mid-season (Table 13).

TABLE 13

Population density, fungal parasitism of eggs and second-stage juveniles (J2) of *Heterodera glycines*, and soybean yield in field plots treated with nematophagous fungi in 1999.

| Agent | Dosage | Eggs/100 cm3 soil: Pi[a] | Eggs/100 cm3 soil: Pm[b] | Eggs/100 cm3 soil: Pf[c] | J2/100 $cm^3$ soil | % J2 Parasitized | EPI[c] | Yield (bu/a) |
|---|---|---|---|---|---|---|---|---|
| | | | | | Steel site | | | |
| *Verticillium chlamydosporium* (*Vc*) | 0.50% | 6,313 | 17,248a[e] | 16,375ab | 1,331ab | 26.5 bcd | 4.1a | 30.8bc |
| ARF18 | 0.50% | 6,000 | 13,761abcd | 9,975b | 856bc | 16.0e | 3.3bc | 30.4bcd |
| *Hirsutella rhossiliensis* (*Hr*) | 0.50% | 6,263 | 15,638abc | 28,025a | 1,094bc | 38.0b | 3.0c | 32.2b |
| *Hirsutella rhossiliensis* (*Hr*) | 0.10% | 6,575 | 18,956a | 20,975a | 1,356ab | 38.0b | 3.4abc | 32.6b |
| *Hirsutella minnesotensis* (*Hm*) | 0.50% | 6,525 | 13,819abc | 13,025ab | 1,238ab | 37.5b | 4.1a | 31.6bc |
| *Hirsutella minnesotensis* (*Hm*) | 0.10% | 6,505 | 17,360a | 15,225ab | 1,714a | 56.5a | 4.1a | 30.2bcde |
| *Vc* + *Hm* | 0.5% + 0.5% | 5,219 | 15,385ab | 14,625ab | 1,160ab | 36.0bc | 3.5abc | 27.5cde |
| *Vc* + *Hr* | 0.5% + 0.5% | 7,090 | 8,900cd | 14,800ab | 998bc | 19.5de | 3.4abc | 31.9b |

TABLE 13-continued

Population density, fungal parasitism of eggs and second-stage juveniles (J2) of *Heterodera glycines*, and soybean yield in field plots treated with nematophagous fungi in 1999.

| Agent | Dosage | Eggs/100 cm3 soil Pi[a] | Pm[b] | Pf[c] | J2/100 $cm^3$ soil | % J2 Parasitized | EPI[c] | Yield (bu/a) |
|---|---|---|---|---|---|---|---|---|
| Temik | 1200 g ai/acre | 6,200 | 7,038d | 15,550ab | 752c | 19.5de | 3.2bc | 30.6bc |
| Resistant cultivar | | 5,915 | 1,425e | 1,538c | 96d | 17.8de | 4.1a | 41.4a |
| Control without agent | | 5,815 | 12,074abc | 15,275ab | 1,318ab | 25.0cde | 4.1a | 31.3bc |
| Control with autoclaved corn grits | 0.50% | 6,220 | 16,365ab | 9,100b | 1,162abc | 23.0de | 3.8abc | 26.3de |
| Control with autoclaved corn grits | 0.10% | 5,513 | 11,413bcd | 14,975ab | 928bc | 17.5de | 3.4abc | 26.1e |
| *Beuveria bassiana* | 0.50% | 5,785 | 17,438a | 15,700ab | 1,046abc | 19.0de | 3.8ab | 31.1bc |
| | | | | | Waseca | | | |
| *Verticillium chlamydosporium* (*Vc*) | 0.50% | 1,383b | 1,172b | 5,400c | 221ab | 1.5ef | 4.1ab | 28.3bcde |
| ARF18 | 0.50% | 2,053ab | 1,466ab | 8,875abc | 221ab | 2.0def | 4.1ab | 31.9abcd |
| *Hirsutella rhossiliensis* (*Hr*) | 0.50% | 2,525ab | 2,535a | 10,150ab | 201abc | 7.0bc | 3.3bc | 34.8abc |
| *Hirsutella rhossiliensis* (*Hr*) | 0.10% | 2,024ab | 2,169ab | 9,300abc | 203abc | 13.0ab | 2.9c | 35.4ab |
| *Hirsutella minnesotensis* (*Hm*) | 0.50% | 3,279a | 1,808ab | 7,000abc | 226abc | 15.5ab | 3.4bc | 33.3abc |
| *Hirsutella minnesotensis* (*Hm*) | 0.10% | 3,210a | 1,194b | 5,800bc | 290a | 18.5a | 3.5bc | 25.3de |
| *Vc* + *Hm* | 0.5% + 0.5% | 1,787ab | 1,634ab | 6,875abc | 145bc | 4.1cde | 3.6abc | 31.1abcd |
| *Vc* + *Hr* | 0.5% + 0.5% | 3,218a | 2,156ab | 7,763bc | 231ab | 5.5cd | 4.1ab | 27.6cde |
| Temik | 1200 g ai/acre | 3,403ab | 1,994ab | 12,100a | 218ab | 2.5cde | 3.5bc | 37.5a |
| Resistant cultivar | | 2,358ab | 1,206ab | 578d | 124c | 3.5de | 4.5a | 31.0abcd |
| Control without agent | | 2,210ab | 2,309ab | 9,700abc | 223ab | 3.0cde | 3.3bc | 24.1de |
| Control with autoclaved corn grits | 0.50% | 3,055a | 1,372ab | 7,900abc | 230ab | 1.5def | 4.2ab | 28.5bcde |
| Control with autoclaved corn grits | 0.10% | 2,757a | 1,525ab | 7,025bc | 227ab | 0.0f | 3.9abc | 27.6cde |
| *Beuveria bassiana* | 0.50% | 1,974ab | 1,575ab | 9,175abc | 259ab | 1.5ef | 3.7abc | 22.2e |

[a]Egg density at planting.
[b]Egg density at 2 months after planting.
[c]Egg density at harvest.
[d]Egg-parasitic index at a scale from 0–10 where 0 = no eggs parasitized by fungi, 1 = 1–10% eggs parasitized, . . . and 10 = 91–100 eggs parasitized by fungi.
[e]Same letter in column indicates no significant difference according LSD at P = 0.05.

Overall control efficiency was lower in 1999 than in 1998. In Steele site, egg density 2 months after planting in plots treated with 0.5% *Verticillium chlamydosporium* and 0.5% of *H. rhossiliensis* was lower than corn-grits control (Table 13). No significant reduction of egg density by other treatments was observed at Waseca and Steele sites. Parasitism of J2 by Hirsutella was observed in all plots in both sites regardless the treatments. Percentage of J2 parasitized by Hirsutella spp., however, was higher in plots treated with *H. rhossiliensis* or *H. minnesotensis* than in plots without the fungal treatment. Treatment with egg-parasitic fungi, *V. chlamydosporium* and ARF18, did not increase egg-parasitic index at mid-season as compared with controls. *Verticillium chlamydosporium* inhibited activity of *H. rhossiliensis* and *H. minnesotensis* and reduced percentage of J2 parasitized by the fungi. Average yield treated with *H. rhossiliensis* (0.1% and 0.5%) was 6.2 and 7.0 bu/A (27% and 25%) higher ($P<0.05$) than average yield of control in Steele and Waseca sites, respectively (Table 13). Average yield treated with *H. minnesotensis* was 4.5 (18%) ($P<0.05$) and 1.3 (4.5%) (not significant) but a higher than control at Steele and Waseca sites, respectively (Table 13). Egg-parasitic fungi did not significantly increase soybean yield. In contrast, mixture of egg-parasitic fungus *V. chlamydosporium* with Hirsutella species reduced control efficiency of Hirsutella species, probably due to competition from *V. chlamydosporium.*

2000 Field Trial

In 2000, one isolated of *H. minnesotensis* and two isolates of *H. rhossiliensis* were tested at one site at Waseca. Other procedures applied in 2000 were the same as used in 1999. At the end of the season, *H. minnesotensis* isolate FA2-1 reduced egg density by 39% (significant at P=0.1 but not at P=0.05), and the *H. rhossiliensis* isolate OWVT-1 reduced egg density by 20% (not significant) (Table 14). No yield increase in treatments with Hirsutella spp. was observed as compared with the control.

TABLE 14

Densities of eggs and second-stage juveniles (J2) of Heterodera glycines and percentage of J2 parasitized by fungi, soybean yield in field plots treated with Hirsutella spp., nematicide, and resistant cultivar in 2000.[a]

| | Eggs/100 cc soil | | | J2/100 cc soil | % J2 parasitizd | Yield |
|---|---|---|---|---|---|---|
| Treatment | At planting | Midseason | At harvest | Midseason | Midseason | bu/A |
| *Hirsutella rhossiliensis* (ATCC46487) | 2,775a | 3,588a | 25,800a | 257a | 5.6b | 45.5b |
| *Hirsutella rhossiliensis* (OWVT-1) | 1,713a | 4,513a | 21,675ab | 270a | 6.4b | 43.8b |
| *Hirsutella minnesotensis* (FA2-1) | 3,097a | 4,138a | 16,725ab | 201a | 14.2a | 44.4b |
| Aldicarb | 2,113a | 1,166bc | 13,975b | 141bc | 12.9a | 55.5a |
| Resistant soybean (Freeborn) | 3,188a | 303c | 879c | 38c | 4.2b | 45.5b |
| Corn-grits control | 1,809a | 3,600a | 27,225a | 161ab | 6.5b | 44.1b |
| Non-amendment control | 3,366a | 3,488ab | 28,025a | 195ab | 5.4b | 45.2b |

[a]Data are the means of four replicates. Values followed by the same letter(s) or without letter in a column are not significantly different at P = 0.05 according to least significant difference test.

EXAMPLE 7

Nutritional Requirement of the Nematophagous Fungus *Hirsutella rhossiliensis*

*Hirsutella rhossitiensis* has potential as a biocontrol agent against plant-parasitic nematodes and its conidia are necessary for infection of the nematode. The nutritional requirement for fungal growth, sporulation and spore germination remains unknown. Six natural media were examined for growth and sporulation of six isolates, and 20 carbohydrates, 18 nitrogen compounds and nine vitamins for growth, sporulation and spore germination of three isolates of *H. rhossiliensis* in solid and/or liquid cultures. VA, CMA and PDA were the best media for the fungal growth and MEA, VA and YDA were the best media for the sporulation. Glycogen was the best carbon source for growth and spore germination of *H. rhossiliensis* in both liquid and solid cultures and followed by sucrose for ATCC46487 and D(+) trehalose for OWVT-1. Inulin, starch soluble, α-cellulose and D(+) trehalose supported good growth for all three isolates. While L-sorbose, D-ribose, citric acid and D-fructose and D(+) galactose reduced the growth of ATCC46487 and OWVT-1 and could not be utilized by JA16-1 on agar. D(+)xylose could not be utilized by all of three isolates on agar and in liquid culture. The best nitrogen sources were casein and peptone for all isolates of *H. rhossiliensis* and L-proline for JA16-1 and L-asparagine, L-aspartic acid, L-histidine, L-lysine, L-proline, L-phenylalanine and DL-serine for ATCC46487 in liquid culture. Casein produced the greatest growth rate for the JA16-1 growth on agar. L-asparagine, peptone and L-proline produced the greatest growth rate for all isolates on agar. L-cystine did not support the growth on agar and in liquid culture for all isolates. DL-methionine, L-phenylalanine, DL-methionine, L-Iysine, ammonium nitrate, glycine and L-histidine were poor nitrogen sources for the fungal growth. Vitamins enhanced the growth and sporulation of *H. rhossiliensis.* The lack of thiamine in the medium with all other vitamins significantly reduced the growth for isolate OWVT-1. Different isolates of *H. rhossiliensis* required different carbon, nitrogen sources and vitamins for sporulation. The best carbohydrates and nitrogen sources for sporulation were D(+)trehalose for isolate ATCC46487, D-sorbitol and DL-threonine for OWVT-1, and D-(+)-cellubiose and L-phenylalanine for JA16-1. Addition of vitamins in media increased the sporulation of *H. rhossiliensis.* The sporulation was enhanced by lack of folic acid and myo-inositol in the media with all other vitamins for ATCC46487, lack of thiamine, folic acid, p-aminobenzoic acid and pyridoxine for OWVT-1 and lack of p-aminobenzoic acid and thiamine for JA16-1 compared to control without any vitamins. The carbohydrates required for germination of *H. rhossiliensis* spores were similar to that for growth. Glycogen was the best carbon source for spore germination, D(+)xylose, L-(−)-sorbose inhibited the spore germination of all isolates. Spore germination of *H. rhossiliensis* was favored by most nitrogen compounds but was significantly inhibited by L-cystine. Lack of riboflavin and myo-inositol in media with all other vitamins significantly increased spore germination of ATCC46487 and OWVT-1 respectively. However, the lack of folic acid, riboflavin, d-biotin and myo-inositol significantly reduced the spore germination of JA16-1.

Fungal growth, sporulation, spore germination may vary among fungi and greatly influenced by media, components of the substrate and culture conditions (Elson et al., 1998; Li & Holdom, 1995; Hayes & Blackburn, 1966; Blackburn & Hayes, 1966). The effects of various carbon and nitrogen sources and vitamins on nematode-trapping fungi have been studied (Blackburn & Hayes, 1966; Bricklebank & Cooke, 1969; Coscarelli & Pramer, 1962; Hayes & Blackburn, 1966; Saxena et al., 1989). *Arthrobotrys oligospora* Fries-enis and *Arthrobotrys robusta* Duddington have simple nutrient requirements, indicating their highly saprophytic ability (Blackburn & Hayes, 1966). In contrast, *Dactylaria bembicodes* Drechsler, a constricting-ring trap-former was unable to utilize either cellulose or starch and inefficient in utilizing glycogen, maltose or sucrose, indicating its poor saprophytic ability (Gray, 1987; Satchuthananthavale & Cooke, 1967a,b). Little is known about the nutritional requirements of nematode-endoparasitic fungi. Parasitism of *Mesocriconema xenoplax* Raski by *H. rhossiliensis* was greatly increased by KCl solution (Jaffee & Zehr, 1983). The endoparasitic fungi *Nematoctonus haptocladus* Drechsler and *Harposporium anguillulae* Zopf were able to grow on simple media containing mineral salts and glucose (Bricklebank & Cooke, 1969).

The objective of this research was to evaluate the effects of common natural media, various carbon and nitrogen sources, and vitamins on the growth, sporulation, and spore germination of *H. rhossiliensis*. The natural media are those that containing natural, biological products. The knowledge of the effects of these nutrients on *H. rhossiliensis* may help understand population dynamics of the fungus in soil and develop strategies for successful application of the fungus as a biological control agent.

Fungal isolates: Six isolates of *H. rhossiliensis* used in the tests on natural media were ATCC46487, OWVT-1, ST3-1, WT21-2, FA2-2, and JA16-1. ATCC46489 was obtained from American Type Culture Collection and originally isolated by from *Mexocriconema xenoplax* collected from Edgefield, S.C. OWVT-1, ST3-1, WT21-2, and FA2-2 were isolated from *H. glycines* J2 collected from Waseca, Steele, Watonwan, and Faribault Counties, respectively, and the isolate JA16-1 was isolated from an unidentified free-living nematode collected from Jackson County during the survey of the fungal parasites of *H. glycines* J2 in Minnesota. The isolates ATCC46487, OWVT-1, and JA16-1 were used in tests for their carbon, nitrogen, and vitamin requirements.

All isolates were preserved on potato dextrose agar (PDA) (Difco, Detroit, Mich.) at 4° C. The fungi were cultured on cornmeal agar (CMA) (Difco, Detroit, Mich.) in 10-cm-diam petri plates before tests on natural media, and cultured on V-8 juice agar (VA) for the carbon, nitrogen and vitamin tests.

Basal mineral medium: The medium designed by Blackbure & Hayes (1966) was used as the basal medium for all tests. The medium was composed of 10 g maltose, 2.0 g $NaNO_3$, 0.5 g $MgSO_4.7H_2O$, 0.5 g $KH_2PO_4$, 0.65 g $Na_2HPO_4$, 0.5 g KCl per liter of distilled water for liquid culture, and these compositions with addition of 17 g Bacto agar (Difco, Detroit, Mich.) for agar tests.

Growth and sporulation of *H. rhossiliensis* on natural media: The six natural media used in this study were PDA, CMA, tryptic soy agar (TSA) (Difco, Detroit, Mich.) malt extract agar (MEA) (Difco, Detroit, Mich.), V-8 juice agar (VA), and yeast dextrose agar (YDA, 1.5% yeast extract, 2% dextrose and 1.7% agar) (MacLeod, 1959), on which growth and sporulation of six isolates of *H. rhossiliensis* were examined. Circular plugs (0.4-cm-diam.) were removed from colony margins of CMA cultures, and one plug per isolate was transferred to the center of each of three plates (10-cm-diam.) for each medium. Plates were sealed with parafilm and incubated at room temperature (22-24° C.). Diameters of the resulting colony were measured weekly up to 5 weeks. To determine sporulation, eight plugs (0.4-cm-diam) were removed from each plate after 5 weeks of incubation and transferred to 10 ml sterile 0.1% Tween-20 surfactant in a 50-ml tube and vigorously agitated on a linear Ebe-back shaker (forward and backward shaker) for 15 minutes to dislodge and suspend the spores. The number of spores per ml was determined with hemacytometer with the aid of microscope at a magnification of 400× (Elson et al., 1998).

Growth of *H. rhossiliensis* isolates from SCN J2 on VA, CMA and PDA were better than that on YDA, MEA and TSA. Growth of isolates of ATCC46487 from *M. xenoplax* and JA16-1 from bacterial-feeding nematode was better on all media except TSA (Table 15). The sporulation of all isolates on MEA, VA and YDA was better than that on PDA and CMA (Table 15). TSA was a poor medium for *H. rhossiliensis* growth and sporulation (Tables 15 and 16). ATCC46487 was the fastest growing isolate on all media except TSA, followed by the isolates from SCN J2. JA16-1 was the slowest growing one on VA, CMA and PDA, but was faster than isolates from SCN J2 on YDA and MEA (Table 15). The spore-producing ability of the isolates was somewhat different between experiment 1 and 2, but isolate JA16-1 from a bacterial-feeding nematode produced more spores than other isolates on all media except TSA in the repeated experiment (Table 15).

TABLE 15

Influence of natural media on the colony growth of *H. rhossiliensis* (mm/day)

| | Test 1 | | | | Test 2 | | | | |
|---|---|---|---|---|---|---|---|---|---|
| Media | OWVT-1 | ST3-1 | JA16-1 | WT21-2 | ATCC** | OWVT-1 | JA16-1 | WT21-2 | FA2-2 |
| VA | 0.82$^{a\ B*}$ | 0.98$^{a\ A}$ | 0.70$^{a\ B}$ | 0.98$^{a\ A}$ | 0.99$^{a\ A}$ | 0.80$^{a\ BC}$ | 0.68$^{bc\ D}$ | 0.84$^{a\ BC}$ | 0.88$^{a\ AB}$ |
| CMA | 0.71$^{b\ B}$ | 0.90$^{ab\ A}$ | 0.68$^{a\ B}$ | 0.90$^{a\ A}$ | 1.04$^{a\ A}$ | 0.58$^{b\ B}$ | 0.60$^{bc\ B}$ | 0.73$^{a\ B}$ | 0.75$^{b\ B}$ |
| PDA | 0.63$^{bc\ C}$ | 0.80$^{b\ AB}$ | 0.71$^{a\ BC}$ | 0.86$^{a\ A}$ | 0.85$^{a\ A}$ | 0.59$^{b\ D}$ | 0.63$^{bc\ CD}$ | 0.82$^{a\ AB}$ | 0.73$^{b\ BC}$ |
| YGA | 0.50$^{cd\ A}$ | 0.52$^{c\ A}$ | 0.67$^{a\ A}$ | 0.51$^{b\ A}$ | 0.92$^{a\ A}$ | 0.48$^{c\ C}$ | 0.75$^{a\ B}$ | 0.50$^{b\ C}$ | 0.52$^{c\ C}$ |
| MEA | 0.46$^{d\ B}$ | 0.50$^{c\ B}$ | 0.73$^{a\ A}$ | 0.49$^{b\ B}$ | 0.95$^{a\ A}$ | 0.40$^{c\ D}$ | 0.73$^{bc\ B}$ | 0.37$^{c\ D}$ | 0.51$^{c\ CD}$ |
| TSA | 0.25$^{e\ BC}$ | 0.18$^{d\ C}$ | 0.36$^{b\ A}$ | 0.30$^{c\ B}$ | 0.29$^{b\ AB}$ | 0.19$^{d\ B}$ | 0.34$^{d\ AB}$ | 0.44$^{bc\ A}$ | 0.24$^{d\ AB}$ |

*Lower case letter indicates the statistical difference within a column (P < 0.001); Uppercase letter shows the statistical difference within a row in each experiment (P < 0.001)
**ATCC = ATCC46487

TABLE 16

Influence of the media on the sporulation of *H. rhossiliensis* (104 spores/cm2)

| | Test 1 | | | | Test 2 | | | |
|---|---|---|---|---|---|---|---|---|
| Media | OWVT-1 | ST3-1 | JA16-1 | WT21-2 | ATCC | OWVT-1 | JA16-1 | FA2-2 |
| MEA | 82.3$^{a\ A}$ | 34.4$^{ab\ C}$ | 30.3$^{ab\ C}$ | 58.5$^{a\ B}$ | 23.0$^{a\ B}$ | 15.2$^{ab\ B}$ | 58.2$^{aA}$ | 21.9$^{aB}$ |
| VA | 23.6$^{b\ A}$ | 44.0$^{a\ A}$ | 38.8$^{a\ A}$ | 37.1$^{b\ A}$ | 14.4$^{b\ C}$ | 17.8$^{a\ BC}$ | 50.3$^{aA}$ | 23.7$^{aB}$ |
| YGA | 16.4$^{bc\ B}$ | 50.8$^{a\ A}$ | 25.9$^{abcB}$ | 43.3$^{abA}$ | 21.9$^{a\ B}$ | 17.7$^{a\ B}$ | 48.3$^{aA}$ | 21.6$^{aB}$ |
| PDA | 14.1$^{bcBC}$ | 23.0$^{b\ AB}$ | 32.3$^{ab\ A}$ | 9.7$^{c\ C}$ | 8.1$^{bcC}$ | 9.2$^{bcBC}$ | 22.7$^{bA}$ | 12.9$^{bB}$ |
| CMA | 4.1$^{c\ B}$ | 17.6$^{bc\ A}$ | 13.1$^{bc\ A}$ | 6.6$^{c\ B}$ | 3.1$^{cdB}$ | 3.3$^{cd\ B}$ | 16.7$^{bA}$ | 4.7$^{cB}$ |
| TSA | 1.5$^{c\ A}$ | 1.0$^{c\ A}$ | 2.1$^{c\ A}$ | 0.4$^{c\ A}$ | 0.7$^{d\ A}$ | 0.0$^{d\ A}$ | 0.6$^{dA}$ | 0.5$^{cA}$ |

*Lowercase letter shows the statistical difference within a column (P < 0.001); uppercase letter shows the statistical difference within a row in each experiment (P < 0.001)
**ATCC = ATCC46487

Effect of carbon source on growth, sporulation and spore germination: Twenty carbohydrates used in the study were listed in Table 17. An amount of 4 g/liter carbon of each of the test carbon sources was added individually into basal medium. NaNO$_3$ at 0.3296 g/L nitrogen was used as the nitrogen source in the carbon study. Control was the medium free of any carbon. Fifteen ml of medium were added to 50-ml plastic tubes for liquid culture and 10-cm-diam petri plates for agar culture.

Inoculum was prepared by washing spores and hyphal fragments from V8juice-agar culture with 0.1% Tween-20 solution and then passed through 40-μm-aperture cell

TABLE 17

Effects of carbon sources on growth rate, sporulation and spore germination of *H. rhossiliensis* on agar and growth rate in liquid culture after incubation for 5 weeks.

| | On agar | | | | | | | | | In liquid culture | | |
|---|---|---|---|---|---|---|---|---|---|---|---|---|
| | Growth mm-in-diam | | | Sporulation 10$^3$/cm$^2$ | | | Spore germination % | | | | | |
| Carbon source | ATCC46487 | OWVT-1 | JA16-1 | ATCC46487 | OWVT-1 | JA16-1 | ATCC46487 | OWVT-1 | JA16-1 | ATCC 46487 | OWVT-1 | JA16-1 |
| D-(−)-arabinose | 18.0A* | 9.7A− | 0.0A− | 22.3 | 35.2 | 27.0 | 48.9 | 40.0 | 32.2 | O | O | O |
| a-cellulose | 33.7A+ | 26.8A+ | 19.0A− | 1.6 | 2.1 | 12.7 | ND | ND | ND | I | I | O |
| D-(+)-cellubiose | 33.0A+ | 12.3A | 10.0A− | 13.8 | 23.9 | 88.8 | 58.9 | 52.2 | 52.2 | I | I | I |
| Citric acid | 11.3A | 9.0A | 0.0A− | 39.5 | 87.5 | 7.4 | 50.0 | 52.2 | 38.9 | II | II | O |
| D(−)fructose | 16.2A | 8.5A− | 0.0A− | 50.2 | 36.8 | 0.0 | 45.6 | 50.0 | 34.4 | I | I | O |
| D(+)galactose | 25.0A+ | 7.0A− | 0.0A− | 2.8 | 7.7 | 7.4 | 62.2 | 43.3 | 43.3 | I | O | O |
| Glycogen | 46.8A++ | 34.8A+ | 20.5A+ | 77.5 | 7.9 | 12.4 | 72.2 | 72.2 | 77.8 | V | IV | IV |
| D-(+)-glucose | 28.3A+ | 8.0A− | 6.5A | 7.7 | 30.7 | 28.1 | 61.1 | 56.7 | 65.5 | I | I | O |
| Inulin | 36.7A | 25.2A | 20.0A | 3.5 | 4.2 | 10.4 | 54.4 | 50.0 | 72.2 | II | II | I |
| a-lactose monohydrate | 35.8A+ | 9.8A− | 15.8A | 2.4 | 17.4 | 37.3 | 56.7 | 42.2 | 68.9 | I | I | I |
| D-mannitol | 29.5A+ | 23.2A | 18.0A | 15.9 | 40.6 | 17.3 | 58.9 | 60.0 | 61.1 | III | II | I |
| Maltose monohydrate | 34.3A+ | 13.7A | 11.0A | 21.9 | 34.2 | 26.6 | 36.7 | 46.7 | 64.5 | I | I | I |
| Melibiose | 35.0A+ | 18.2A | 11.8A | 41.9 | 33.7 | 13.1 | 40.0 | 48.9 | 61.7 | III | II | I |
| D(−)ribose | 15.5A | 8.0A− | 0.0A− | 61.3 | 1.4 | 0.0 | 48.9 | 45.6 | 15.5 | O | O | O |
| D-sorbitol | 30.3A+ | 11.7A+ | 18.3A | 64.7 | 126.0 | 4.2 | 57.8 | 56.7 | 67.8 | III | II | I |
| L-(−)-sorbose | 7.8A | 6.7A− | 0.0A− | 62.5 | 7.4 | 0.0 | 35.6 | 26.7 | 13.3 | I | I | O |
| Starch soluble | 33.0A++ | 25.0A+ | 19.3A | 20.1 | 6.5 | 5.0 | 47.8 | 58.9 | 76.7 | IV | III | III |
| Sucrose | 39.5A+ | 21.8A+ | 15.0A | 38.9 | 47.7 | 6.9 | 55.6 | 52.2 | 73.4 | III | II | I |
| D(+) trehalose | 36.5A++ | 30.2A+ | 18.3A | 172.6 | 49.2 | 5.2 | 60.0 | 62.2 | 68.9 | ND | ND | ND |
| D(+)xylose | 0.0A− | 0.0A− | 0.0A− | 0.0 | 0.0 | 2.5 | 21.1 | 26.7 | 24.4 | O | O | O |
| CK (no carbon) | 35.0A− | 26.3A | 18.3A− | 1.1 | 3.5 | 0.0 | 55.6 | 48.9 | 60.0 | I | I | I |
| LSD (P < 0.01) | 2.1 | 2.8 | 1.4 | 33.1 | 38.6 | 34.0 | 12.2 | 13.0 | 11.7 | | | |

*A− = No aerial mycelium, A = little aerial mycelium, A+ = average aerial mycelium, A++ = rich in aerial mycelium
**Visual measure standard: O = no visible growth; I: little growth (separated hyphae), no significant colony formed; II = small separated colonies or hyphal mass formed; III = hyphae growth or colonies form a pellet, less than 2.5 ml; IV = the pellet diameter larger than 1 cm, but the total volume distribution less than 5 ml.
ND = not data strainer (Falcon, Fisher Scientific). Fifty μl fungal spore and mycelium suspension were used as inoculum for the liquid culture and 10 μl for the agar culture. After incubation for 24 hr, 30 spores were randomly observed for germination on the agar culture. Colony forming unites (cfu) originated from the spores and/or hyphal fragments in the suspension were determined. The plates and tubes were incubated at room temperature for 5 weeks, and then growth was estimated by visual ratings and colony diameters. The visual ratings for growth on agar were: 0=no aerial mycelium; 1=little aerial mycelium; 2=a fair amount of aerial mycelium; and 3=abundant arial mycelium. The visual ratings for growth in liquid culture were: 0=no visible growth; 1=a little growth with separated hyphae, but no colony formed; 2=small separated colonies or hyphal mass formed; 3=hyphae grew or colonies joined together to form pellets, and total volume of pellets was less than 2.5 ml; 4=pellet diameters were larger than 1 cm, and total volume of the pellets was more than 5 ml; 5=hyphal mass was more than 5 ml. The colony diameter was measured after 5 weeks for the agar culture, and then 1 ml of 0.1% Tween-20 solution was added onto each colony to wash the spores into a 1.5-ml centrifuge tube. Spores were counted by using hemacytometer with the aid of microscope, and the number of spores per square centimeter was determined (Elson et al., 1998). Growth of fungi on some media was not measurable, but spores were produced in the area of inoculation (approximately 0.6 cm in diam). The sporulation per square centimeter was calculated from the inoculation area in this situation.

Glycogen was the best carbon source for growth of *H. rhossiliensis* among 20 carbon compounds tested in both liquid and solid cultures and followed by sucrose for ATCC46487 and D(+) trehalose for OWVT-1. Inulin, starch soluble, α-cellulose, and D(+)trehalose supported good growth for all three isolates. The good growth was supported by α-lactose monohydrate, melibiose, maltose monohydrate and D-(+)-cellubiose for ATCC46487, D-mannitol, sucrose and melibiose for OWVT-1 and D-sorbitol, and D-mannitol, α-lactose monohydrate, and sucrose for JA16-1. While L-sorbose, D-ribose, citric acid and D-fructose and D(+) galactose were poor carbon source for ATCC46487 and OWVT-1 and could not be utilized by JA16-1 on agar. D(+)xylose could not be utilized by all isolates on agar and in liquid culture, and D-(−)-arabinose and D(−) ribose could not be utilized in liquid culture. Growth of *H. rhossiliensis* on control without any addition of carbohydrates was fastest on the solid media, but the resultant colony was quite sparse (Table 17).

Effect of nitrogen source on growth, sporulation and spore germination: Eighteen nitrogen compounds were used in his study (Table 18). Sucrose at 4 g/L carbon was used as the carbon source for the nitrogen study. Experimental procedures were the same as that employed in the carbon study, except that the amount of each nitrogen source was calculated so as to provide nitrogen of 0.3296 g/L. Controls were the medium without nitrogen and the medium without both nitrogen and carbon.

TABLE 18

Effects of the nitrogen sources on growth rate, sporulation and spore germination of *H. rhossiliensis* on agar and growth rate in liquid culture after incubation for 5 weeks.

| | On agar | | | | | | | | | | | |
|---|---|---|---|---|---|---|---|---|---|---|---|---|
| | Growth mm-in-diam | | | Sporulation $10^3/cm^2$ | | | Spore germination % | | | In liquid culture | | |
| Nitrogen source | ATCC46487 | OWVT-1 | JA16-1 | ATCC 46487 | OWVT-1 | JA16-1 | ATCC 46487 | OWVT-1 | JA16-1 | ATCC 46487 | OWVT-1 | JA16-1 |
| $NaNO_3$ | 39.2A+* | 21.7A | 15.3A− | 10.0 | 35.9 | 6.4 | 86.7 | 55.6 | 73.3 | IV | II | I |
| L-Arginine | 42.8A+ | 19.5A | 15.8A | 3.5 | 19.1 | 1.4 | 91.1 | 76.7 | 86.6 | V | III | IV |
| L-Asparagine | 51.8A+ | 20.8A | 16.5A | 4.5 | 18.7 | 8.3 | 93.3 | 70.0 | 85.5 | VI | III | IV |
| L-Aspartic acid | 43.8A+ | 16.8A | 13.3A+ | 5.2 | 3.6 | 10.9 | 93.3 | 53.3 | 90.0 | VI | III | IV |
| Casein | NDA++ | 23.0A | NDA | ND | 43.6 | ND | 96.7 | 44.4 | 90.0 | VI | V | V |
| L-cystine | 0.0 | 0.0 | 0.0 | 12.3 | 0.0 | 3.9 | 14.4 | 5.6 | 4.4 | O | O | O |
| Glycine | 41.5A++ | 10.7A+ | 7.5A | 10.2 | 33.9 | 1.3 | 75.6 | 60.0 | 93.3 | VI | III | III |
| DL-Glutamic acid | 40.8A+ | 18.7A | 12.8A+ | 8.7 | 2.6 | 29.8 | 74.4 | 48.9 | 90.0 | VI | III | V |
| L-Histidine | 36.3A++ | 12.8A+ | 8.5A− | 1.8 | 2.1 | 3.4 | 82.2 | 65.6 | 82.2 | V | III | II |
| L-Lysine | 31.9A+ | 9.3A− | 9.8A− | 1.7 | 0.0 | 2.1 | 86.7 | 50.0 | 90.0 | IV | III | III |
| DL-Methionine | 11.7A | 0.0 | 0.0 | 3.2 | 0.0 | 10.8 | 74.4 | 63.3 | 70.0 | III | I | I |
| Peptone | 46.2A++ | 16.8A | 24.8A+ | 6.2 | 13.9 | 15.5 | 96.7 | 66.7 | 92.2 | VI | V | V |
| L-proline | 47.2A+ | 23.8A− | 17.0A | 7.3 | 9.6 | 30.9 | 86.7 | 60.0 | 86.7 | VI | III | V |
| L-Phenylalanine | 34.3A+ | 17.5A+ | 11.7A | 7.9 | 15.9 | 79.0 | 77.8 | 68.3 | 86.7 | VI | IV | O |
| DL-Serine | 45.3A++ | 17.2A | 10.2A | 7.9 | 3.1 | 2.4 | 84.4 | 72.2 | 87.8 | VI | IV | III |
| DL-Threonine | 25.4A++ | 9.0A− | 8.3A− | 13.8 | 136.5 | 26.4 | 93.3 | 48.9 | 83.3 | V | III | IV |
| L-tyrosine | 35.7A+ | 19.3A | 15.7A | 15.4 | 22.4 | 31.2 | 91.1 | 67.8 | 86.7 | V | II | III |
| Urea | 43.5A+ | 16.7A | 14.0A+ | 5.2 | 10.6 | 0.4 | 91.1 | 64.4 | 85.6 | IV | II | II |
| Ammonium nitrate | 35.7A++ | 17.2A+ | 11.0A− | 10.3 | 4.6 | 2.3 | 93.3 | 57.8 | 91.1 | V | III | III |
| CK(no N) | 29.8A+ | 25.3A+ | 13.7A++ | 0.5 | 22.3 | 41.7 | 73.3 | 71.1 | 87.8 | I | I | I |

TABLE 18-continued

Effects of the nitrogen sources on growth rate, sporulation and spore germination of *H. rhossiliensis* on agar and growth rate in liquid culture after incubation for 5 weeks.

| Nitrogen source | On agar: Growth mm-in-diam ATCC46487 | OWVT-1 | JA16-1 | Sporulation $10^3/cm^2$ ATCC 46487 | OWVT-1 | JA16-1 | Spore germination % ATCC 46487 | OWVT-1 | JA16-1 | In liquid culture ATCC 46487 | OWVT-1 | JA16-1 |
|---|---|---|---|---|---|---|---|---|---|---|---|---|
| CK(no N & C) | 42.8A− | 24.7A− | 17.5A− | 5.6 | 3.7 | 13.3 | 85.6 | 45.6 | 81.1 | O | O | O |
| LSD (P <0.01) | 5.7 | 3.2 | 2.1 | 9.5 | 25.8 | 39.7 | 8.9 | 12.9 | 8.3 | | | |

*The standard used was the same as carbon study.
**The standard used was the same as carbon study.
ND = not data The nitrogen compounds resulting in the faster growth in both liquid and agar cultures were casein and peptone for all isolates of *H. rhossiliensis,* and L-proline for JA16-1 and L-asparagine, L-aspartic acid, L-histidine, L-lysine, L-proline, L-phenylalanine and DL-serine for ATCC46487 in liquid culture. Peptone was the best for the JA16-1 growth on agar. L-asparagine and L-proline were the best nitrogen sources for all isolates on agar. Casein supported good growth, although the data for ATCC46487 and JA16-1 were not included because the inoculum drop on agar spread out. L-cystine could not be utilized by all isolates on agar and in liquid culture. DL-methionine could not be utilized by OWVT-1 and JA16-1 and inhibited ATCC46487 growth on agar. L-phenylalanine could not be utilized by JA16-1 in liquid culture. DL-methionine and L-lysine reduced the growth of all isolates. Ammonium nitrate inhibited ATCC46487 growth and glycine and L-histidine inhibited the growth of OWVT-1 and JA16-1 (Table 18).

Sporulation was affected by different nitrogen sources for the three isolates. The best nitrogen compounds for sporulation were DL-threonine for OWVT-1 and L-phenylalanine for JA16-1. L-tyrosine, DL-threonine supported better sporulation of ATCC46487 but not significantly different from control without nitrogen (Table 18). Spore germination of all isolates was well supported by most nitrogen compounds but were significantly inhibited by L-cystine (Table 18).

Effect of vitamin on growth, sporulation and spore germination: Nine vitamins were used in this study (Table 19). Vitamin requirement was determined by excluding one vitamin at each time from the basal medium plus all test vitamins. All of the vitamins selected were added to the basal medium at 200 $\mu$g/L except that biotin and myo-inositol were added at 5 $\mu$g/L and 5 mg/L, respectively. Thiamin and 4-aminobenzoic acid were sterilized by filtering with a 0.45-$\mu$-aperture filter (Fisher, Scientific) and added to the sterile medium. Other vitamins were added into the medium prior to heat sterilization. Controls were the medium with all vitamins and the medium without any vitamins (Saxena et al., 1989). Sucrose at 4 g/L carbon and $NaNO_3$ at 0.3296 g/L nitrogen were used as the carbon and nitrogen sources, respectively, in the vitamin study. Other procedures of the experiment were the same as used in the carbon study.

TABLE 19

Effects of the vitamins on growth rate, sporulation and spore germination of *H. rhossiliensis* on agar and growth rate in liquid culture after incubation for 5 weeks.

| Vitamin excluded | On agar: Growth rate mm-in-diam ATCC 46487 | OWVT-1 | JAl6-1 | Sporulation $10^3/cm^2$ ATCC 46487 | OWVT-1 | JA16-1 | Spore germination % ATCC 46487 | OWVT-1 | JA16-1 | In liquid culture ATCC 46487 | OWVT-1 | JA16-1 |
|---|---|---|---|---|---|---|---|---|---|---|---|---|
| p-Amino-benzoic acid (PABA) | 41.5A++* | 28.3A+ | 16.7A+ | 29.9 | 14.2 | 35.1 | 82.2 | 51.1 | 84.4 | II** | II | I |
| d-Biotin (V.H) | 39.7A++ | 27.7A+ | 16.3A+ | 29.5 | 11.7 | 14.1 | 80.0 | 50.0 | 90.0 | II | II | I |
| Folic acid | 39.3A++ | 28.7A+ | 19.7A+ | 59.7 | 15.4 | 24.2 | 82.2 | 61.1 | 87.8 | II | II | I |
| myo-inositol | 40.8A++ | 31.5A+ | 18.3A+ | 41.9 | 8.3 | 16.7 | 72.2 | 64.4 | 84.4 | II | II | I |
| Nicotinic acid | 40.5A++ | 27.7A+ | 20.0A+ | 30.1 | 10.7 | 12.2 | 77.8 | 57.8 | 94.4 | II | II | I |

TABLE 19-continued

Effects of the vitamins on growth rate, sporulation and spore germination of *H. rhossiliensis* on agar and growth rate in liquid culture after incubation for 5 weeks.

| | On agar | | | | | | | | | | | |
|---|---|---|---|---|---|---|---|---|---|---|---|---|
| | Growth rate mm-in-diam | | | Sporulation $10^3/cm^2$ | | | Spore germination % | | | In liquid culture | | |
| Vitamin excluded | ATCC 46487 | OWVT-1 | JA16-1 | ATCC 46487 | OWVT-1 | JA16-1 | ATCC 46487 | OWVT-1 | JA16-1 | ATCC 46487 | OWVT-1 | JA16-1 |
| DL-pantothenic acid | 39.5A++ | 29.3A+ | 18.8A+ | 28.6 | 9.9 | 17.1 | 72.2 | 55.6 | 88.9 | II | II | I |
| Pyridoxine (VB6) | 40.5A++ | 29.5A+ | 17.2A+ | 31.1 | 13.0 | 16.5 | 74.4 | 50.0 | 90.0 | III | II | I |
| Riboflavin, UPS (VB2) | 41.0A++ | 30.2A+ | 20.2A+ | 30.6 | 11.1 | 13.2 | 91.1 | 60.0 | 85.6 | II | I | I |
| Thiamine (VB1) | 38.5A++ | 24.7A+ | 20.3A+ | 30.1 | 15.7 | 30.4 | 75.6 | 58.9 | 91.1 | II | II | II |
| CK (all Vitamins) | 39.3A++ | 28.7A+ | 18.8A+ | 28.2 | 9.9 | 22.6 | 77.8 | 55.6 | 93.3 | II | II | II |
| CK (no Vitamins) | 38.5A++ | 21.8A | 15.5A+ | 16.3 | 6.2 | 4.4 | 71.1 | 43.3 | 88.9 | II | II | I |
| LSD ($P < 0.01$) | 5.2 | 2.7 | 5.6 | 19.4 | 6.4 | 22.2 | 8.4 | 7.4 | 4.4 | | | |

*The standard used was the same as carbon study.
**The standard used was the same as carbon study.

All vitamins promoted OWVT-1 growth significantly. Lack of thiamine in the medium with all other vitamins significantly reduced the growth in OWVT-1. The vitamins seemed increase the growth of ATCC46487 and JA16-1 but were not statistically significant (Table 19).

Addition of vitamins in the media generally increased the sporulation of all isolates but was not statistically significant. The sporulation was enhanced by lack of folic acid and myo-inositol for ATCC46487. Lack of thiamine, folic acid, p-aminobenzoic acid and pyridoxine increased sporulation of OWVT-1 and lack of p-aminobenzoic acid and thiamine increased sporulation of JA16-1 (Table 19).

The lack of riboflavin and myo-inositol in the media with all other vitamins significantly increased spore germination of ATCC46487 and OWVT-1 respectively. However, the lack of folic acid, riboflavin, d-biotin and myo-inositol significantly reduced spore germination of JA16-1 (Table 19).

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

LITERATURE CITED

Blackburn, F. and Hayes, W. A. (1966). Studies on the nutrition of *Arthrobotrys oligospora* Fres. and *A. robusta* Dudd. I. The saprophytic phase. *Annual Applied Biology* 58, 43–50.

Blackburn, F. and Hayes, W. A. (1966). Studies on the nutrition of *Arthrobotrys oligospora* Fres. and *A. robusta* Dudd. I. The saprophytic phase. *Annual Applied Biology* 58, 43–50.

Bourne, J. M., B. R. Kerry, and F. A. A. M. De Leij. 1996. The importance of the host plant on the interaction between root-knot nematodes (Meloidogyne spp.) and the nematophagous fungus, *Verticillium chlamydosporium* Goddard. Biocontrol Science & Technology 6:539–548.

Carneiro, R. M. D. G., and C. B. Gomes. 1993. Methodology and pathogenicity tests effect of *Paecilomyces litacinus* and *P. fumosoroseus* isolates to eggs of *Meloidogyne javanica*. Nematologia Brasileira 17:66–75.

Cayrol, J. C., Castet, R., and Samson, R. A. 1986. Comparative activity of different Hirsutella species towards three plant parasitic nematodes. *Rev. Nematol.* 9:412–414.

Cayrol, J. C., and Frankowski, J. P. 1986. Influence of the number of parasitizing conidia of *Hirsutella rhossiliensis* on the mortality of *Ditylenchus dipsaci. Rev. Nematol.* 9:411–412.

Cayrol, J. C., and Combettes, S. 1983. Study of the aggressiveness of some nematophagous fungi toward *Anguina agrostis. Rev. Nematol.* 6:153–154.

Chen, S. Y. 1997. Infection of *Heterodera glycines* by *Hirsutella rhossiliensis* in a Minnesota soybean field. Journal of Nematology 29:573.

Chen, S. Y., X. Z. Liu, and F. J. Chen. 2000. *Hirsutella minnesotensis* sp. nov.—a new pathogen of the soybean cyst nematode. Mycologia 92:819–824.

Ciancio, A., Logrieco, A., and Lamberti, F. 1986. Parasitism of *Xiphinema diversicaudatum* by the fungus *Hirsutella rhossiliensis. Nematol. Mediterranea* 14:187–192.

Coscarelli, W. and Pramer, D. (1962). Nutrition and growth of *Arthrobotrys conoides. Journal of Bacteriology* 84, 60–64.

Dickie, G. A., and C. R. Bell. 1995. A full factorial analysis of nine factors influencing in vitro antagonistic screens for potential biocontrol agents. Canadian Journal of Microbiology 41:284–293.

Drechsler, C. 1941. Some hyphomycetes parasitic on free-living terricolous nematodes. *Phytopathology* 31:773–801.

Elson, M. K., Schisler, D. A. and Jackson, M. A. (1998). Carbon-to-nitrogen ratio, carbon concentration, and amino acid composition of growth media influence conidiation of *Helminthosporium solani. Mycologia* 98,406–413.

Galper, S., L. M. Eden, G. R. Stirling, and L. J. Smith. 1995. Simple screening methods for assessing the predacious activity of nematode-trapping fungi. Nematologica 41:130–140.

Gray, N. F. (1987). Nematophagous fungi with special reference to their ecology. *Biological Review* 62, 245–304.

Hayes, W. A. and Blackburn, F. (1966). Studies on the nutrition of *Arthrobotrys oligospora* Fres. and *A. robusta* Dudd. II. The predaceous phase. *Annual Applied Biology* 58, 51–60.

Irving, F., and B. R. Kerry. 1987. Variation between strains of the nematophagous fungus, *Verticillium chlamydosporium* Goddard. II. Factors affecting parasitism of cyst nematode eggs. Nematologica 32:474–485.

Jaffee, B. A., and Zehr, E. I. 1982. Parasitism of the nematode *Criconemella xenoplax* by the fungus *Hirsutella rhossiliensis*. *Phytopathology* 72:1378–1381.

Jaffee, B. A. and E. I. Zehr. 1983. Effects of certain solutes, osmotic potential, and soil solutions on parasitism of *Criconemella xenoplax* by *Hirsutella rhossiliensis*. Phytopathology 73:544–546.

Jaffee, B. A., and E. I. Zehr. 1985. Parasitic and saprophytic abilities of the nematode-attacking fungus *Hirsutella rhossiliensis*. Journal of Nematology 17:341–345.

Jaffee, B. A., Gaspard, J. T., Ferris, H., and Muldoon, A. E. 1988. Quantification of parasitism of the soil-borne nematode *Criconemella xenoplar* by the nematophagous fungus *Hirsutella rhossiliensis*. *Soil Biol. Biochem.* 20:631–636.

Jaffee, B. A., J. T. Gaspard, and H. Ferris. 1989. Density-dependent parasitism of the soil-borne nematode *Criconemella xennoplax* by *Hirsutella rhossiliensis*. Microbial Ecology 17:193–200.

Jaffee, B. A., and Muldoon, A. E. 1989. Suppression of cyst nematode by natural infestation of a nematophagous fungus. *J. of Nematol.* 21:505–510.

Jaffee, B. A., A. E. Muldoon, R. Phillips, and M. Mangel. 1990. Rates of spore transmission, mortality, and production for the nematophagous fungus *Hirsutella rhossiliensis*. Phytopathology 80:1083–1088.

Jaffee, B. A., A. E. Muldoon, C. E. Anderson, and B. B. Westerdahl. 1991. Detection of the nematophagous fungus *Hirsutella rhossiliensis* in California sugarbeet fields. Biological Control 1:63–67.

Jaffee, B. A., Phillips, R., Muldoon, A. E., and Mangel, M. 1992. Density-dependent host pathogen dynamics in soil microcosms. *Ecology* 73:495–506.

Jaffee, B. A., H. Ferris, J. J. Stapleton, M. V. K. Norton, and A. E. Muldoon. 1994. Parasitism of nematodes by the fungus *Hirsutella rhossiliensis* as affected by certain organic amendments. Journal of Nematology 26:152–161.

Jaffee, B. A., A. E. Muldoon, and B. B. Westerdahl. 1996. Failure of a mycelial formulation of the nematophagous fungus *Hirsutella rhossiliensis* to suppress the nematode *Heterodera schachtii*. Biological Control 6:340–346.

Jenkins, W. R. 1964. A rapid centrifugal-flotation technique for separating nematodes from soil. Plant Disease Report 48:692.

Juhl, M. 1985. The effect of *Hirsutella heteroderae* on the multiplication of the beet cyst nematode on sugar beet. *Tidsskr. Planteavl* 89:475–480.

Lackey, B. A., A. E. Muldoon, and B. A. Jaffee. 1993. Alginate pellet formulation of *Hirsutella rhossiliensis* for biological control of plant-parasitic nematodes. Biological Control 3:155–160.

Li, D. P. and Holdom, D. G. (1995). Effects of nutrients on colony formation, growth, and sporulation of *Metarhizium anisopliae* (Deuteromycotina: Hyphomycetes). *Journal of Invertebrate Pathology* 65, 253–260.

Linford, M. B. 1937. Stimulated activity of natural enemies of nematodes. Science 85:123–124.

Liu, X. Z., and S. Y. Chen. 2000a. Parasitism of *Heterodera glycines* by Hirsutella spp. in Minnesota soybean fields. Biological Control 19:161–166.

Liu, X. Z., and S. Y. Chen. 2000b. Screening isolates of Hirsutella species for biocontrol of *Heterodera glycines*. Biocontrol and Technology:in press.

MacLeod, D. M. (1959). Nutritional studies on the genus Hirsutella I. Growth response in an enriched liquid medium. *Canadian Journal of Botany* 37, 695–714.

McInnis, T. M., and B. A. Jaffee. 1989. An assay for *Hirsutella rhossiliensis* spores and the importance of phialides for nematode inoculation. Journal of Nematology 21:229–234.

Minter, D. W. and B. L. Brady. 1980. Mononematous species of Hirsutella. Transactions of the British Mycological Society 74:271–282.

Müller, J. 1982. The influence of fungal parasites on the population dynamics of *Heterodera schachtii* on oil radish. *Nematologica* 28:161.

Müller, J. 1984. The influence of two pesticides on fungal parasites of *Heterodera schachtii*. *Les Colloques de l'INRA* 31:225–231.

Müller, J. 1986. Prospects and limits of biological control of nematodes in sugar beet. *J. Landwirtsc. Forsch.* 37:333–341.

Noel, G. R. 1992. History, distribution, and economics. Pp. 1–13 in R. D. Riggs and J. A. Wrather eds. Biology and management of the soybean cyst nematode. St. Paul, Minn.: APS Press.

Satchuthananthavale, V., and Cooke, R. C. (1967a). Carbohydrate nutrition of some nematode-trapping fungi. *Nature* 214, 321–322.

Satchuthananthavale, V. & Cooke, R. C. (1967b). Nitrogen nutrition of some nematode-trapping fungi. *Transactions of the British Mycological Society* 50,423–428.

Saxena, G., R. Dayal, and Mukeiji, K. G. (1989). Nutritional studies on nematode-trapping fungi. *Folia Microbiology.* 34,42–48.

Smolik, J. D. 1996. First report of *Heterodera glycines* on soybean in South Dakota. *Plant Dis.* 80:224.

Stirling, G. R., and Kerry, B. R. 1983. Antagonists of the cereal cyst nematode *Heterodera avenae* Woll. in Australia soils. *Australia J. of Exp. Agri. and Animal Husbandry* 23:318–324.

Stirling, G. R. 1991. Biological control of plant parasitic nematodes. Wallingford, U. K.: CAB International.

Sturhan, D., and R. Schneider. 1980. *Hirsutella heteroderae*, a new nematode-parasitic fungus. Phytopathologische Zeitschrift 99:105–115.

Tedford, E. C., B. A. Jaffee, A. E. Muldoon, C. E. Anderson, and B. B. Westerdahl. 1993. Parasitism of *Heterodera schachtii* and *Meloidogyne javanica* by *Hirsutella rhossiliensis* in microplots over two growing seasons. Journal of Nematology 25:427–433.

Tedford, E. C., B. A. Jaffee, and A. E. Muldoon. 1994. Variability among isolates of the nematophagous fungus *Hirsutella rhossiliensis*. Mycological Research 98:1127–1136.

Timper, P., Kaya, H. K., and Jaffee, B. A. 1991. Survival of entomogenous nematodes in soil infested with the nematode-parasitic fungus *Hirsutella rhossiliensis* (Deuteromycotina: Hyphomycetes). *Biological Control* 1:42–50.

Timper, P., and B. B. Brodie. 1993. Infection of *Pratylenchus penetrans* by nematode-pathogenic fungi. Journal of Nematol. 25:297–302.

Timper, P., and R. D. Riggs. 1998. Variation in efficacy of isolates of the fungus ARF against the soybean cyst nematode *Heterodera glycines*. Journal of Nematology 30:461–467.

Velvis, H., and P. Kamp. 1995. Infection of second-stage juveniles of potato cyst nematodes by the nematophagous fungus *Hirsutella rhossiliensis* in Dutch potato fields. Nematologica 41:617–627.

Velvis, H. and P. Kamp. 1996. Suppression of potato cyst nematode root penetration by the endoparasitic nematophagous fungi *Hirsutella rhossiliensis*. European Journal of Plant Pathology 102:115–122.

Waller, P. J., and M. Faedo. 1993. The potential of nematophagous fungi to control the free-living stages of nematode parasites of sheep: Screening studies. Veterinary Parasitology 49:285–297.

Zehr, E. I. 1985. Evaluation of parasites and predators of plant parasitic nematodes. Journal of Agricultural Entomology 2:130–134.

Zopf, W. 1888. Zur kenntis der infections-krenkheiten niederer thiere und pflanzen. Nova acta Academiae Caesareae Leopoldino Canaliae gernanicae naturae curiosonum 52:314–376.

What is claimed is:

1. A biologically pure culture of *Hirsutella minnesotensis*, wherein the *H. minnesotensis* is culture deposit ATCC PTA 3180.

2. A pesticidal composition comprising an effective amount of a biologically pure culture of a fungal strain, wherein the fungal strain is *Hirsutella minnesotensis* capable of controlling nematode infestation and a carrier, wherein the *H. minnesotensis is culture deposit ATCC PTA* 3180.

3. A method for controlling nematodes comprising applying an effective amount of a pesticidal composition into soil before planting, or onto a target plant or onto the situs of a target plant, wherein the pesticidal composition comprises an effective amount of a biologically pure culture of a fungal strain, wherein the fungal strain is *Hirsutella minnesotensis* capable of controlling nematode infestation and a carrier, wherein *H. minnesotensis* is culture deposit ATCC PTA 3180.

* * * * *